(12) United States Patent
Andre et al.

(10) Patent No.: US 10,711,063 B2
(45) Date of Patent: Jul. 14, 2020

(54) NEUTRALIZATION OF INHIBITORY PATHWAYS IN LYMPHOCYTES

(71) Applicant: INNATE PHARMA, Marseilles (FR)

(72) Inventors: Pascale Andre, Marseilles (FR); Mathieu Blery, Marseilles (FR); Carine Paturel, Marcy l'Etoile (FR); Nicolai Wagtmann, Cassis (FR)

(73) Assignee: INNATE PHARMA, Marseilles (FR)

( * ) Notice: Subject to any disclaimer, the term of this patent is extended or adjusted under 35 U.S.C. 154(b) by 378 days.

(21) Appl. No.: 15/511,778

(22) PCT Filed: Sep. 15, 2015

(86) PCT No.: PCT/EP2015/071069
§ 371 (c)(1),
(2) Date: Mar. 16, 2017

(87) PCT Pub. No.: WO2016/041945
PCT Pub. Date: Mar. 24, 2016

(65) Prior Publication Data
US 2017/0291947 A1   Oct. 12, 2017

Related U.S. Application Data

(60) Provisional application No. 62/050,948, filed on Sep. 16, 2014, provisional application No. 62/083,929, filed on Nov. 25, 2014, provisional application No. 62/093,141, filed on Dec. 17, 2014.

(51) Int. Cl.
| | |
|---|---|
| A61K 39/395 | (2006.01) |
| C07K 16/28 | (2006.01) |
| C07K 16/30 | (2006.01) |
| A61K 39/00 | (2006.01) |

(52) U.S. Cl.
CPC .... *C07K 16/2818* (2013.01); *A61K 39/39558* (2013.01); *C07K 16/2803* (2013.01); *C07K 16/2827* (2013.01); *C07K 16/30* (2013.01); *A61K 2039/507* (2013.01); *A61K 2039/545* (2013.01); *C07K 2317/565* (2013.01); *C07K 2317/76* (2013.01)

(58) Field of Classification Search
None
See application file for complete search history.

(56) References Cited

U.S. PATENT DOCUMENTS

| | | |
|---|---|---|
| 8,206,709 B2 | 6/2012 | Spee et al. |
| 8,796,427 B2 | 8/2014 | Spee et al. |
| 8,901,283 B2 | 12/2014 | Spee et al. |
| 8,993,319 B2 | 3/2015 | Moretta et al. |
| 9,422,368 B2 | 8/2016 | Spee et al. |
| 9,512,228 B2 | 12/2016 | Soederstroem et al. |
| 9,683,041 B2 | 6/2017 | Spee et al. |
| 9,795,674 B2 | 10/2017 | Parshad et al. |
| 10,160,810 B2 | 12/2018 | Moretta et al. |
| 10,329,348 B2 | 6/2019 | Andre et al. |
| 2017/0073417 A1 | 3/2017 | Soederstroem et al. |
| 2017/0253658 A1 | 9/2017 | Van der Burg et al. |
| 2017/0298131 A1 | 10/2017 | Andre et al. |
| 2017/0313773 A1 | 11/2017 | Andre et al. |
| 2018/0000935 A1 | 1/2018 | Parshad |
| 2019/0031755 A1 | 1/2019 | Andre et al. |
| 2019/0135938 A1 | 5/2019 | Moretta et al. |
| 2019/0248896 A1 | 8/2019 | Spee et al. |

FOREIGN PATENT DOCUMENTS

WO   WO 2016/041947   3/2016

OTHER PUBLICATIONS

Katou et al. (Cancer Res 2007, 67 (23) pp. 11195-11201) (Year: 2007).*
Perez-Gracia et al. (Current Opinion in Immunology, vol. 27, Apr. 1, 2014, p. 89-97). (Year: 2014).*
Written Opinion in International Application No. PCT/EP2015/071069, dated Jan. 11, 2016, pp. 1-7.
Katou, F. et al. "Differing Phenotypes between Intraepithelial and Stromal Lymphocytes in Early-Stage Tongue Cancer" *Cancer Research*, Dec. 1, 2007, pp. 11195-11201, vol. 67, No. 23.
Perez-Garcia, J. L. et al. "Orchestrating immune check-point blockade for cancer in combinations" *Current Opinion in Immunology*, Apr. 1, 2014, pp. 89-97, vol. 27.
Anonymous, "Astrazeneca Innate au crible de Invest Securities: recommandation positive" *Blog Biotech Finances*, Apr. 27, 2015, pp. 1-7, retrieved from the Internet: URL:http://blog.biotech-finances.com/astrazeneca-innate-au-crible-de-invest-securities/ on Dec. 8, 2015, XP002752006.
Anonymous, "Innate Pharma et AstraZeneca annoncent un accord global de Co-Devéloppment et de commercialization pour iph2201 en Immuno-Oncologie" *Zonebourse*, Apr. 24, 2015, retrieved from the Internet: URL:http://www.zonebourse.com/Innate-Phama-35620/actualite/Innate-Pharma--et-AstraZeneca-annoncent-un-accord-global-pour-IPH2201-en-immuno-oncologie-20250055/ on Dec. 8, 2015, XP002752007.
Claims as filed for U.S. Appl. No. 16/226,742, 2018, pp. 1-3.
Currently pending claims of U.S. Appl. No. 16/448,016, 2019, pp. 1-3.

* cited by examiner

*Primary Examiner* — Meera Natarajan
(74) *Attorney, Agent, or Firm* — Saliwanchik, Lloyd & Eisenschenk

(57) ABSTRACT

The present invention relates to methods for the treatment, prevention and diagnostic of diseases using compounds that specifically bind and inhibit human NKG2A in combination with compounds that bind and inhibit human PD-1. The invention also relates to assays to identify NKG2A+PD1+ tumor infiltrating NK and/or CD8 T cells.

13 Claims, 7 Drawing Sheets
Specification includes a Sequence Listing.

Tumor cells

Tumor infiltrating lymphocytes

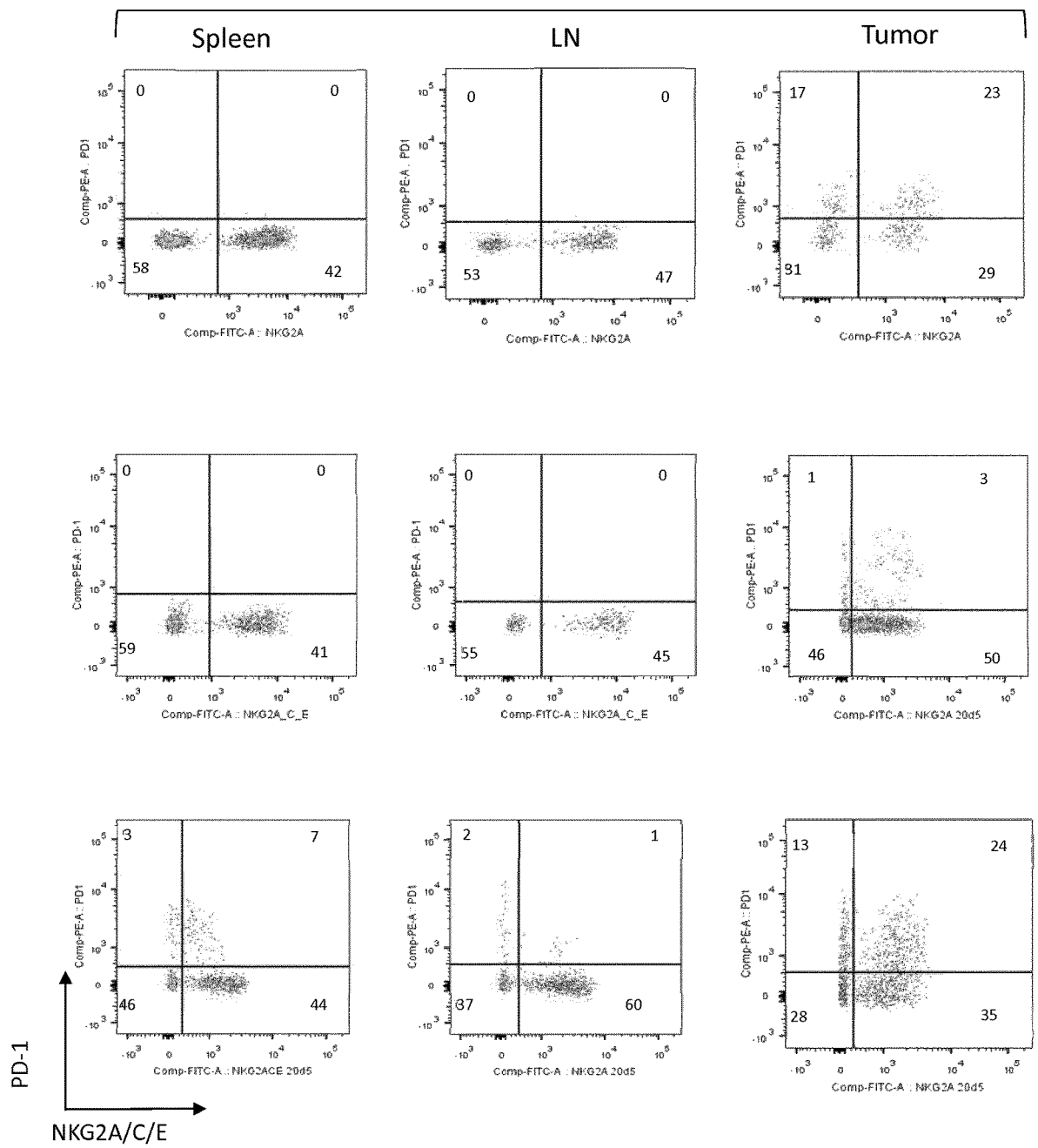

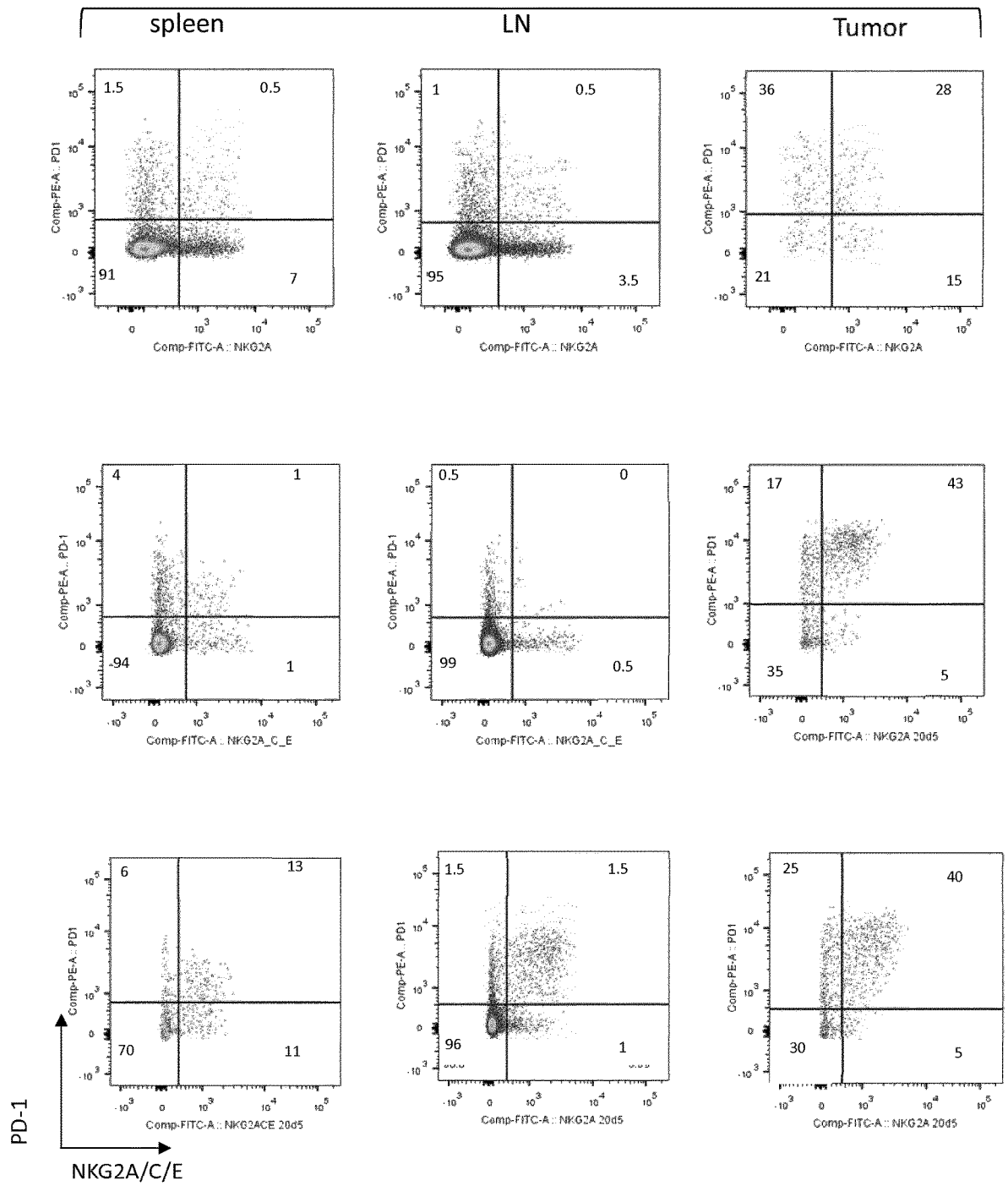

SEQUENCE LISTING

<160> NUMBER OF SEQ ID NOS: 15

<210> SEQ ID NO 1
<211> LENGTH: 233
<212> TYPE: PRT
<213> ORGANISM: Homo sapiens

<400> SEQUENCE: 1

```
Met Asp Asn Gln Gly Val Ile Tyr Ser Asp Leu Asn Leu Pro Pro Asn
1               5                   10                  15

Pro Lys Arg Gln Gln Arg Lys Pro Lys Gly Asn Lys Ser Ser Ile Leu
            20                  25                  30

Ala Thr Glu Gln Glu Ile Thr Tyr Ala Glu Leu Asn Leu Gln Lys Ala
        35                  40                  45

Ser Gln Asp Phe Gln Gly Asn Asp Lys Thr Tyr His Cys Lys Asp Leu
    50                  55                  60

Pro Ser Ala Pro Glu Lys Leu Ile Val Gly Ile Leu Gly Ile Ile Cys
65                  70                  75                  80

Leu Ile Leu Met Ala Ser Val Val Thr Ile Val Val Ile Pro Ser Thr
                85                  90                  95

Leu Ile Gln Arg His Asn Asn Ser Ser Leu Asn Thr Arg Thr Gln Lys
```

```
                100              105              110
Ala Arg His Cys Gly His Cys Pro Glu Glu Trp Ile Thr Tyr Ser Asn
            115              120              125

Ser Cys Tyr Tyr Ile Gly Lys Glu Arg Arg Thr Trp Glu Glu Ser Leu
        130              135              140

Leu Ala Cys Thr Ser Lys Asn Ser Ser Leu Leu Ser Ile Asp Asn Glu
145              150              155              160

Glu Glu Met Lys Phe Leu Ser Ile Ile Ser Pro Ser Ser Trp Ile Gly
                165              170              175

Val Phe Arg Asn Ser Ser His His Pro Trp Val Thr Met Asn Gly Leu
            180              185              190

Ala Phe Lys His Glu Ile Lys Asp Ser Asp Asn Ala Glu Leu Asn Cys
        195              200              205

Ala Val Leu Gln Val Asn Arg Leu Lys Ser Ala Gln Cys Gly Ser Ser
            210              215              220

Ile Ile Tyr His Cys Lys His Lys Leu
225              230

<210> SEQ ID NO 2
<211> LENGTH: 288
<212> TYPE: PRT
<213> ORGANISM: Homo sapiens

<400> SEQUENCE: 2

Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
                20                  25                  30

Asn Pro Pro Thr Phe Phe Pro Ala Leu Leu Val Val Thr Glu Gly Asp
            35                  40                  45

Asn Ala Thr Phe Thr Cys Ser Phe Ser Asn Thr Ser Glu Ser Phe Val
50                  55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Gln Asp Cys Arg Phe Arg
                85                  90                  95

Val Thr Gln Leu Pro Asn Gly Arg Asp Phe His Met Ser Val Val Arg
            100                 105                 110

Ala Arg Arg Asn Asp Ser Gly Thr Tyr Leu Cys Gly Ala Ile Ser Leu
        115                 120                 125

Ala Pro Lys Ala Gln Ile Lys Glu Ser Leu Arg Ala Glu Leu Arg Val
    130                 135                 140

Thr Glu Arg Arg Ala Glu Val Pro Thr Ala His Pro Ser Pro Ser Pro
145                 150                 155                 160

Arg Pro Ala Gly Gln Phe Gln Thr Leu Val Val Gly Val Val Gly Gly
                165                 170                 175

Leu Leu Gly Ser Leu Val Leu Leu Val Trp Val Leu Ala Val Ile Cys
            180                 185                 190

Ser Arg Ala Ala Arg Gly Thr Ile Gly Ala Arg Arg Thr Gly Gln Pro
        195                 200                 205

Leu Lys Glu Asp Pro Ser Ala Val Pro Val Phe Ser Val Asp Tyr Gly
    210                 215                 220

Glu Leu Asp Phe Gln Trp Arg Glu Lys Thr Pro Glu Pro Pro Val Pro
225                 230                 235                 240
```

```
Cys Val Pro Glu Gln Thr Glu Tyr Ala Thr Ile Val Phe Pro Ser Gly
                245                 250                 255

Met Gly Thr Ser Ser Pro Ala Arg Arg Gly Ser Ala Asp Gly Pro Arg
                260                 265                 270

Ser Ala Gln Pro Leu Arg Pro Glu Asp Gly His Cys Ser Trp Pro Leu
                275                 280                 285

<210> SEQ ID NO 3
<211> LENGTH: 290
<212> TYPE: PRT
<213> ORGANISM: Homo sapiens

<400> SEQUENCE: 3

Met Arg Ile Phe Ala Val Phe Ile Phe Met Thr Tyr Trp His Leu Leu
1               5                   10                  15

Asn Ala Phe Thr Val Thr Val Pro Lys Asp Leu Tyr Val Val Glu Tyr
                20                  25                  30

Gly Ser Asn Met Thr Ile Glu Cys Lys Phe Pro Val Glu Lys Gln Leu
            35                  40                  45

Asp Leu Ala Ala Leu Ile Val Tyr Trp Glu Met Glu Asp Lys Asn Ile
        50                  55                  60

Ile Gln Phe Val His Gly Glu Glu Asp Leu Lys Val Gln His Ser Ser
65                  70                  75                  80

Tyr Arg Gln Arg Ala Arg Leu Leu Lys Asp Gln Leu Ser Leu Gly Asn
                85                  90                  95

Ala Ala Leu Gln Ile Thr Asp Val Lys Leu Gln Asp Ala Gly Val Tyr
            100                 105                 110

Arg Cys Met Ile Ser Tyr Gly Gly Ala Asp Tyr Lys Arg Ile Thr Val
        115                 120                 125

Lys Val Asn Ala Pro Tyr Asn Lys Ile Asn Gln Arg Ile Leu Val Val
130                 135                 140

Asp Pro Val Thr Ser Glu His Glu Leu Thr Cys Gln Ala Glu Gly Tyr
145                 150                 155                 160

Pro Lys Ala Glu Val Ile Trp Thr Ser Ser Asp His Gln Val Leu Ser
                165                 170                 175

Gly Lys Thr Thr Thr Thr Asn Ser Lys Arg Glu Glu Lys Leu Phe Asn
            180                 185                 190

Val Thr Ser Thr Leu Arg Ile Asn Thr Thr Thr Asn Glu Ile Phe Tyr
        195                 200                 205

Cys Thr Phe Arg Arg Leu Asp Pro Glu Glu Asn His Thr Ala Glu Leu
    210                 215                 220

Val Ile Pro Glu Leu Pro Leu Ala His Pro Pro Asn Glu Arg Thr His
225                 230                 235                 240

Leu Val Ile Leu Gly Ala Ile Leu Leu Cys Leu Gly Val Ala Leu Thr
                245                 250                 255

Phe Ile Phe Arg Leu Arg Lys Gly Arg Met Met Asp Val Lys Lys Cys
                260                 265                 270

Gly Ile Gln Asp Thr Asn Ser Lys Lys Gln Ser Asp Thr His Leu Glu
            275                 280                 285

Glu Thr
    290

<210> SEQ ID NO 4
<211> LENGTH: 452
<212> TYPE: PRT
<213> ORGANISM: Artificial
```

```
<220> FEATURE:
<223> OTHER INFORMATION: Chimeric human-mouse

<400> SEQUENCE: 4

Glu Val Gln Leu Val Gln Ser Gly Ala Glu Val Lys Pro Gly Glu
1               5                   10                  15

Ser Leu Lys Ile Ser Cys Lys Gly Ser Gly Tyr Ser Phe Thr Ser Tyr
            20                  25                  30

Trp Met Asn Trp Val Arg Gln Met Pro Gly Lys Gly Leu Glu Trp Met
        35                  40                  45

Gly Arg Ile Asp Pro Tyr Asp Ser Glu Thr His Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Gly Gly Tyr Asp Phe Asp Val Gly Thr Leu Tyr Trp Phe Phe
            100                 105                 110

Asp Val Trp Gly Gln Gly Thr Thr Val Thr Val Ser Ser Ala Ser Thr
        115                 120                 125

Lys Gly Pro Ser Val Phe Pro Leu Ala Pro Cys Ser Arg Ser Thr Ser
130                 135                 140

Glu Ser Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Leu Gly Thr Lys Thr Tyr Thr Cys
        195                 200                 205

Asn Val Asp His Lys Pro Ser Asn Thr Lys Val Asp Lys Arg Val Glu
    210                 215                 220

Ser Lys Tyr Gly Pro Pro Cys Pro Pro Cys Pro Ala Pro Glu Phe Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

Gln Glu Asp Pro Glu Val Gln Phe Asn Trp Tyr Val Asp Gly Val Glu
        275                 280                 285

Val His Asn Ala Lys Thr Lys Pro Arg Glu Glu Gln Phe Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Gly Leu Pro Ser Ser
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Gln Glu Glu Met Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400
```

-continued

```
Pro Val Leu Asp Ser Asp Gly Ser Phe Phe Leu Tyr Ser Arg Leu Thr
            405                 410                 415
Val Asp Lys Ser Arg Trp Gln Glu Gly Asn Val Phe Ser Cys Ser Val
            420                 425                 430
Met His Glu Ala Leu His Asn His Tyr Thr Gln Lys Ser Leu Ser Leu
            435                 440                 445
Ser Leu Gly Lys
    450

<210> SEQ ID NO 5
<211> LENGTH: 452
<212> TYPE: PRT
<213> ORGANISM: Artificial
<220> FEATURE:
<223> OTHER INFORMATION: Chimeric human-mouse

<400> SEQUENCE: 5

Gln Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Thr Ser Tyr
            20                  25                  30
Trp Met Asn Trp Val Arg Gln Ala Pro Gly Gln Gly Leu Glu Trp Met
        35                  40                  45
Gly Arg Ile Asp Pro Tyr Asp Ser Glu Thr His Tyr Ala Gln Lys Leu
    50                  55                  60
Gln Gly Arg Val Thr Met Thr Thr Asp Thr Ser Thr Ser Thr Ala Tyr
65                  70                  75                  80
Met Glu Leu Arg Ser Leu Arg Ser Asp Asp Thr Ala Val Tyr Tyr Cys
                85                  90                  95
Ala Arg Gly Gly Tyr Asp Phe Asp Val Gly Thr Leu Tyr Trp Phe Phe
            100                 105                 110
Asp Val Trp Gly Gln Gly Thr Thr Val Thr Val Ser Ser Ala Ser Thr
            115                 120                 125
Lys Gly Pro Ser Val Phe Pro Leu Ala Pro Cys Ser Arg Ser Thr Ser
    130                 135                 140
Glu Ser Thr Ala Ala Leu Gly Cys Leu Val Lys Asp Tyr Phe Pro Glu
145                 150                 155                 160
Pro Val Thr Val Ser Trp Asn Ser Gly Ala Leu Thr Ser Gly Val His
                165                 170                 175
Thr Phe Pro Ala Val Leu Gln Ser Ser Gly Leu Tyr Ser Leu Ser Ser
            180                 185                 190
Val Val Thr Val Pro Ser Ser Ser Leu Gly Thr Lys Thr Tyr Thr Cys
            195                 200                 205
Asn Val Asp His Lys Pro Ser Asn Thr Lys Val Asp Lys Arg Val Glu
    210                 215                 220
Ser Lys Tyr Gly Pro Pro Cys Pro Pro Cys Pro Ala Pro Glu Phe Leu
225                 230                 235                 240
Gly Gly Pro Ser Val Phe Leu Phe Pro Pro Lys Pro Lys Asp Thr Leu
                245                 250                 255
Met Ile Ser Arg Thr Pro Glu Val Thr Cys Val Val Val Asp Val Ser
            260                 265                 270
Gln Glu Asp Pro Glu Val Gln Phe Asn Trp Tyr Val Asp Gly Val Glu
            275                 280                 285
Val His Asn Ala Lys Thr Lys Pro Arg Glu Glu Gln Phe Asn Ser Thr
    290                 295                 300
```

```
Tyr Arg Val Val Ser Val Leu Thr Val Leu His Gln Asp Trp Leu Asn
305                 310                 315                 320

Gly Lys Glu Tyr Lys Cys Lys Val Ser Asn Lys Gly Leu Pro Ser Ser
            325                 330                 335

Ile Glu Lys Thr Ile Ser Lys Ala Lys Gly Gln Pro Arg Glu Pro Gln
            340                 345                 350

Val Tyr Thr Leu Pro Pro Ser Gln Glu Glu Met Thr Lys Asn Gln Val
            355                 360                 365

Ser Leu Thr Cys Leu Val Lys Gly Phe Tyr Pro Ser Asp Ile Ala Val
370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Arg Leu Thr
                405                 410                 415

Val Asp Lys Ser Arg Trp Gln Glu Gly Asn Val Phe Ser Cys Ser Val
            420                 425                 430

Met His Glu Ala Leu His Asn His Tyr Thr Gln Lys Ser Leu Ser Leu
            435                 440                 445

Ser Leu Gly Lys
    450

<210> SEQ ID NO 6
<211> LENGTH: 452
<212> TYPE: PRT
<213> ORGANISM: Artificial
<220> FEATURE:
<223> OTHER INFORMATION: chimeric human-mouse

<400> SEQUENCE: 6

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Ser Phe Thr Ser Tyr
            20                  25                  30

Trp Met Asn Trp Val Arg Gln Met Pro Gly Lys Gly Leu Glu Trp Met
        35                  40                  45

Gly Arg Ile Asp Pro Tyr Asp Ser Glu Thr His Tyr Ser Pro Ser Phe
50                  55                  60

Gln Gly His Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
            85                  90                  95

Ala Arg Gly Gly Tyr Asp Phe Asp Val Gly Thr Leu Tyr Trp Phe Phe
            100                 105                 110

Asp Val Trp Gly Gln Gly Thr Thr Val Thr Val Ser Ser Ala Ser Thr
            115                 120                 125

Lys Gly Pro Ser Val Phe Pro Leu Ala Pro Cys Ser Arg Ser Thr Ser
130                 135                 140

Glu Ser Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
            165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Lys Thr Tyr Thr Cys
            195                 200                 205
```

Asn Val Asp His Lys Pro Ser Asn Thr Lys Val Asp Lys Arg Val Glu
            210                 215                 220

Ser Lys Tyr Gly Pro Pro Cys Pro Pro Cys Pro Ala Pro Glu Phe Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

Gln Glu Asp Pro Glu Val Gln Phe Asn Trp Tyr Val Asp Gly Val Glu
        275                 280                 285

Val His Asn Ala Lys Thr Lys Pro Arg Glu Glu Gln Phe Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Gly Leu Pro Ser Ser
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Gln Glu Glu Met Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Arg Leu Thr
                405                 410                 415

Val Asp Lys Ser Arg Trp Gln Glu Gly Asn Val Phe Ser Cys Ser Val
            420                 425                 430

Met His Glu Ala Leu His Asn His Tyr Thr Gln Lys Ser Leu Ser Leu
        435                 440                 445

Ser Leu Gly Lys
    450

<210> SEQ ID NO 7
<211> LENGTH: 452
<212> TYPE: PRT
<213> ORGANISM: Artificial
<220> FEATURE:
<223> OTHER INFORMATION: Chimeric human-mouse

<400> SEQUENCE: 7

Glu Val Gln Leu Val Gln Ser Gly Ala Glu Val Lys Lys Pro Gly Ala
1               5                   10                  15

Thr Val Lys Ile Ser Cys Lys Val Ser Gly Tyr Thr Phe Thr Ser Tyr
            20                  25                  30

Trp Met Asn Trp Val Gln Gln Ala Pro Gly Lys Gly Leu Glu Trp Met
        35                  40                  45

Gly Arg Ile Asp Pro Tyr Asp Ser Glu Thr His Tyr Ala Glu Lys Phe
    50                  55                  60

Gln Gly Arg Val Thr Ile Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Thr Gly Gly Tyr Asp Phe Asp Val Gly Thr Leu Tyr Trp Phe Phe
            100                 105                 110

```
Asp Val Trp Gly Gln Gly Thr Thr Val Thr Val Ser Ser Ala Ser Thr
            115                 120                 125

Lys Gly Pro Ser Val Phe Pro Leu Ala Pro Cys Ser Arg Ser Thr Ser
        130                 135                 140

Glu Ser Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Leu Gly Thr Lys Thr Tyr Thr Cys
        195                 200                 205

Asn Val Asp His Lys Pro Ser Asn Thr Lys Val Asp Lys Arg Val Glu
        210                 215                 220

Ser Lys Tyr Gly Pro Pro Cys Pro Pro Cys Pro Ala Pro Glu Phe Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

Gln Glu Asp Pro Glu Val Gln Phe Asn Trp Tyr Val Asp Gly Val Glu
        275                 280                 285

Val His Asn Ala Lys Thr Lys Pro Arg Glu Glu Gln Phe Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Gly Leu Pro Ser Ser
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Gln Glu Glu Met Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Arg Leu Thr
                405                 410                 415

Val Asp Lys Ser Arg Trp Gln Glu Gly Asn Val Phe Ser Cys Ser Val
            420                 425                 430

Met His Glu Ala Leu His Asn His Tyr Thr Gln Lys Ser Leu Ser Leu
        435                 440                 445

Ser Leu Gly Lys
    450

<210> SEQ ID NO 8
<211> LENGTH: 452
<212> TYPE: PRT
<213> ORGANISM: Artificial
<220> FEATURE:
<223> OTHER INFORMATION: Chimeric human-mouse

<400> SEQUENCE: 8

Gln Val Gln Leu Val Gln Ser Gly Ala Glu Val Lys Lys Pro Gly Ala
1               5                   10                  15
```

-continued

```
Ser Val Lys Val Ser Cys Lys Ala Ser Gly Tyr Thr Phe Thr Ser Tyr
            20                  25                  30
Trp Met Asn Trp Val Arg Gln Ala Pro Gly Gln Gly Leu Glu Trp Met
        35                  40                  45
Gly Arg Ile Asp Pro Tyr Asp Ser Glu Thr His Tyr Ala Gln Lys Phe
 50                  55                  60
Gln Gly Arg Val Thr Met Thr Arg Asp Thr Ser Thr Ser Thr Val Tyr
 65                  70                  75                  80
Met Glu Leu Ser Ser Leu Arg Ser Glu Asp Thr Ala Val Tyr Tyr Cys
                85                  90                  95
Ala Arg Gly Gly Tyr Asp Phe Asp Val Gly Thr Leu Tyr Trp Phe Phe
            100                 105                 110
Asp Val Trp Gly Gln Gly Thr Thr Val Thr Val Ser Ser Ala Ser Thr
        115                 120                 125
Lys Gly Pro Ser Val Phe Pro Leu Ala Pro Cys Ser Arg Ser Thr Ser
130                 135                 140
Glu Ser Thr Ala Ala Leu Gly Cys Leu Val Lys Asp Tyr Phe Pro Glu
145                 150                 155                 160
Pro Val Thr Val Ser Trp Asn Ser Gly Ala Leu Thr Ser Gly Val His
                165                 170                 175
Thr Phe Pro Ala Val Leu Gln Ser Ser Gly Leu Tyr Ser Leu Ser Ser
            180                 185                 190
Val Val Thr Val Pro Ser Ser Ser Leu Gly Thr Lys Thr Tyr Thr Cys
        195                 200                 205
Asn Val Asp His Lys Pro Ser Asn Thr Lys Val Asp Lys Arg Val Glu
    210                 215                 220
Ser Lys Tyr Gly Pro Pro Cys Pro Pro Cys Pro Ala Pro Glu Phe Leu
225                 230                 235                 240
Gly Gly Pro Ser Val Phe Leu Phe Pro Pro Lys Pro Lys Asp Thr Leu
                245                 250                 255
Met Ile Ser Arg Thr Pro Glu Val Thr Cys Val Val Val Asp Val Ser
            260                 265                 270
Gln Glu Asp Pro Glu Val Gln Phe Asn Trp Tyr Val Asp Gly Val Glu
        275                 280                 285
Val His Asn Ala Lys Thr Lys Pro Arg Glu Glu Gln Phe Asn Ser Thr
    290                 295                 300
Tyr Arg Val Val Ser Val Leu Thr Val Leu His Gln Asp Trp Leu Asn
305                 310                 315                 320
Gly Lys Glu Tyr Lys Cys Lys Val Ser Asn Lys Gly Leu Pro Ser Ser
                325                 330                 335
Ile Glu Lys Thr Ile Ser Lys Ala Lys Gly Gln Pro Arg Glu Pro Gln
            340                 345                 350
Val Tyr Thr Leu Pro Pro Ser Gln Glu Glu Met Thr Lys Asn Gln Val
        355                 360                 365
Ser Leu Thr Cys Leu Val Lys Gly Phe Tyr Pro Ser Asp Ile Ala Val
    370                 375                 380
Glu Trp Glu Ser Asn Gly Gln Pro Glu Asn Asn Tyr Lys Thr Thr Pro
385                 390                 395                 400
Pro Val Leu Asp Ser Asp Gly Ser Phe Phe Leu Tyr Ser Arg Leu Thr
                405                 410                 415
Val Asp Lys Ser Arg Trp Gln Glu Gly Asn Val Phe Ser Cys Ser Val
            420                 425                 430
```

Met His Glu Ala Leu His Asn His Tyr Thr Gln Lys Ser Leu Ser Leu
            435                 440                 445

Ser Leu Gly Lys
    450

<210> SEQ ID NO 9
<211> LENGTH: 214
<212> TYPE: PRT
<213> ORGANISM: Artificial
<220> FEATURE:
<223> OTHER INFORMATION: Chimeric human-mouse

<400> SEQUENCE: 9

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asn Ile Tyr Ser Tyr
            20                  25                  30

Leu Ala Trp Tyr Gln Gln Lys Pro Gly Lys Ala Pro Lys Leu Leu Ile
        35                  40                  45

Tyr Asn Ala Lys Thr Leu Ala Glu Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His His Tyr Gly Thr Pro Arg
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 10
<211> LENGTH: 119
<212> TYPE: PRT
<213> ORGANISM: Artificial
<220> FEATURE:
<223> OTHER INFORMATION: Chimeric human-mouse

<400> SEQUENCE: 10

Glu Val Gln Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Ser Tyr
            20                  25                  30

Ala Met Ser Trp Val Arg Gln Ser Pro Glu Lys Arg Leu Glu Trp Val
        35                  40                  45

Ala Glu Ile Ser Ser Gly Gly Ser Tyr Thr Tyr Tyr Pro Asp Thr Val
    50                  55                  60

```
Thr Gly Arg Phe Thr Ile Ser Arg Asp Asn Ala Lys Asn Thr Leu Tyr
 65                  70                  75                  80

Leu Glu Ile Ser Ser Leu Arg Ser Glu Asp Thr Ala Met Tyr Tyr Cys
                 85                  90                  95

Thr Arg His Gly Asp Tyr Pro Arg Phe Phe Asp Val Trp Gly Ala Gly
            100                 105                 110

Thr Thr Val Thr Val Ser Ser
            115

<210> SEQ ID NO 11
<211> LENGTH: 107
<212> TYPE: PRT
<213> ORGANISM: Artificial
<220> FEATURE:
<223> OTHER INFORMATION: Chimeric human-mouse

<400> SEQUENCE: 11

Gln Ile Val Leu Thr Gln Ser Pro Ala Leu Met Ser Ala Ser Pro Gly
  1               5                  10                  15

Glu Lys Val Thr Met Thr Cys Ser Ala Ser Ser Ser Val Ser Tyr Ile
                 20                  25                  30

Tyr Trp Tyr Gln Gln Lys Pro Arg Ser Ser Pro Lys Pro Trp Ile Tyr
             35                  40                  45

Leu Thr Ser Asn Leu Ala Ser Gly Val Pro Ala Arg Phe Ser Gly Ser
 50                  55                  60

Gly Ser Gly Thr Ser Tyr Ser Leu Thr Ile Ser Ser Met Glu Ala Glu
 65                  70                  75                  80

Asp Ala Ala Thr Tyr Tyr Cys Gln Gln Trp Ser Gly Asn Pro Tyr Thr
                 85                  90                  95

Phe Gly Gly Gly Thr Lys Leu Glu Ile Lys Arg
            100                 105

<210> SEQ ID NO 12
<211> LENGTH: 432
<212> TYPE: PRT
<213> ORGANISM: homo sapiens

<400> SEQUENCE: 12

Gln Val Gln Leu Val Glu Ser Gly Gly Gly Trp Gln Pro Gly Arg Ser
  1               5                  10                  15

Leu Arg Leu Asp Cys Lys Ala Ser Gly Ile Thr Phe Ser Asn Ser Gly
                 20                  25                  30

Met His Trp Val Arg Gln Ala Pro Gly Lys Gly Leu Glu Trp Val Ala
             35                  40                  45

Val Arg Trp Tyr Asp Gly Ser Lys Arg Tyr Tyr Ala Asp Ser Val Lys
 50                  55                  60

Gly Arg Phe Thr Ile Ser Arg Asp Asn Ser Lys Asn Thr Leu Phe Leu
 65                  70                  75                  80

Gln Met Asn Ser Leu Arg Ala Glu Asp Thr Ala Val Tyr Tyr Cys Ala
                 85                  90                  95

Thr Asn Asp Asp Tyr Trp Gly Gln Gly Thr Leu Val Thr Val Ser Ser
            100                 105                 110

Ala Ser Thr Lys Gly Pro Ser Val Phe Pro Leu Ala Pro Cys Ser Arg
            115                 120                 125

Ser Thr Ser Glu Ser Thr Ala Ala Leu Gly Cys Leu Val Asp Tyr Phe
        130                 135                 140
```

```
Pro Glu Pro Val Thr Val Ser Trp Asn Ser Gly Ala Leu Thr Ser Gly
145                 150                 155                 160

Val His Thr Phe Pro Ala Val Leu Gln Ser Ser Gly Leu Tyr Ser Leu
                165                 170                 175

Ser Ser Val Val Thr Val Pro Ser Ser Ser Leu Gly Thr Thr Tyr Thr
            180                 185                 190

Cys Asn Val Asp His Lys Pro Ser Asn Thr Lys Val Asp Arg Val Glu
        195                 200                 205

Ser Tyr Gly Pro Pro Cys Pro Pro Cys Pro Ala Pro Glu Phe Leu Gly
    210                 215                 220

Gly Pro Ser Val Phe Leu Phe Pro Pro Lys Pro Lys Asp Thr Leu Met
225                 230                 235                 240

Ile Ser Arg Thr Pro Glu Val Thr Cys Val Val Val Asp Val Ser Gln Glu
                245                 250                 255

Asp Pro Glu Val Gln Phe Asn Trp Tyr Val Asp Gly Val Glu Val His
                260                 265                 270

Asn Ala Thr Lys Pro Arg Glu Glu Gln Phe Asn Ser Thr Tyr Arg Val
            275                 280                 285

Val Ser Val Leu Thr Val Leu His Gln Asp Trp Leu Asn Gly Lys Glu
290                 295                 300

Tyr Lys Cys Lys Val Ser Asn Lys Gly Leu Pro Ser Ser Ile Glu Lys
305                 310                 315                 320

Thr Ile Ser Lys Ala Gly Gln Pro Arg Glu Pro Gln Val Tyr Thr Leu
                325                 330                 335

Pro Pro Ser Gln Glu Glu Met Thr Lys Asn Gln Val Ser Leu Thr Cys
            340                 345                 350

Leu Val Lys Gly Phe Tyr Pro Ser Asp Ile Ala Val Glu Trp Glu Ser
            355                 360                 365

Asn Gly Gln Pro Glu Lys Asn Tyr Lys Thr Thr Pro Pro Val Leu Asp
370                 375                 380

Ser Asp Gly Ser Phe Phe Leu Tyr Ser Arg Leu Thr Val Asp Lys Ser
385                 390                 395                 400

Arg Trp Gln Glu Gly Asn Val Phe Ser Cys Ser Val Met His Glu Ala
                405                 410                 415

Leu His Asn His Tyr Thr Gln Lys Ser Leu Ser Leu Ser Leu Gly Lys
            420                 425                 430

<210> SEQ ID NO 13
<211> LENGTH: 207
<212> TYPE: PRT
<213> ORGANISM: Homo sapiens

<400> SEQUENCE: 13

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Pro Gly Gln Ala Pro Arg Leu Leu Ile Tyr
        35                  40                  45

Asp Ala Ser Asn Arg Ala Thr Gly Ile Pro Ala Arg Phe Ser Gly Ser
    50                  55                  60

Gly Ser Gly Thr Asp Phe Thr Leu Thr Ile Ser Ser Leu Glu Pro Glu
65                  70                  75                  80

Asp Phe Ala Val Tyr Tyr Cys Gln Gln Ser Ser Asn Trp Pro Arg Thr
                85                  90                  95
```

```
Phe Gly Gln Gly Thr Lys Val Glu Ile Arg Thr Val Ala Ala Pro Ser
                100                 105                 110

Val Phe Ile Phe Pro Pro Ser Asp Glu Gln Leu Ser Gly Thr Ala Ser
            115                 120                 125

Val Val Cys Leu Leu Asn Asn Phe Tyr Pro Arg Glu Ala Val Gln Trp
    130                 135                 140

Lys Val Asp Asn Ala Leu Gln Ser Gly Asn Ser Gln Glu Ser Val Thr
145                 150                 155                 160

Glu Gln Asp Ser Asp Ser Thr Tyr Ser Leu Ser Ser Thr Leu Leu Ser
                165                 170                 175

Lys Ala Asp Tyr Glu Lys His Lys Val Tyr Ala Cys Glu Val Thr His
            180                 185                 190

Gln Gly Leu Ser Ser Pro Val Thr Ser Phe Asn Arg Gly Glu Cys
        195                 200                 205

<210> SEQ ID NO 14
<211> LENGTH: 117
<212> TYPE: PRT
<213> ORGANISM: Homo sapiens

<400> SEQUENCE: 14

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ser
            20                  25                  30

Trp Ile His Trp Val Arg Gln Ala Pro Gly Lys Gly Leu Glu Trp Val
        35                  40                  45

Ala Trp Ile Ser Pro Tyr Gly Gly Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Asn Ser Leu Arg Ala Glu Asp Thr Ala Val Tyr Tyr Cys Ala
                85                  90                  95

Arg Arg His Trp Pro Gly Gly Phe Asp Tyr Trp Gly Gln Gly Thr Leu
            100                 105                 110

Val Thr Val Ser Ser
        115

<210> SEQ ID NO 15
<211> LENGTH: 107
<212> TYPE: PRT
<213> ORGANISM: Homo sapiens

<400> SEQUENCE: 15

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Pro Gly Lys Ala Pro Lys Leu Leu Ile Tyr
        35                  40                  45

Ser Ala Ser Phe Leu Tyr Ser Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Tyr Leu Tyr His Pro Ala Thr
                85                  90                  95
```

```
Phe Gly Gln Gly Thr Lys Val Glu Ile Lys Arg
            100                 105
```

NEUTRALIZATION OF INHIBITORY PATHWAYS IN LYMPHOCYTES

CROSS-REFERENCE TO RELATED APPLICATIONS

This application is the U.S. national stage application of International Patent Application No. PCT/EP2015/071069, filed Sep. 15, 2015, which claims the benefit of U.S. Provisional Application Nos. 62/050,948, filed Sep. 16, 2014; 62/083,929 filed Nov. 25, 2014; and 62/093,141 filed Dec. 17, 2014; all of which are incorporated herein by reference in their entirety; including any drawings.

REFERENCE TO SEQUENCE LISTING

The present application is being filed along with a Sequence Listing in electronic format. The Sequence Listing is provided as a file entitled "NKG2A-PD1_ST25", created 15 Sep. 2015, which is 38 KB in size. The information in the electronic format of the Sequence Listing is incorporated herein by reference in its entirety.

FIELD OF THE INVENTION

This invention relates to the combined use of NKG2A-neutralizing agents and PD-1 neutralizing agents for the treatment of cancer.

BACKGROUND OF THE INVENTION

NK cell activity is regulated by a complex mechanism that involves both activating and inhibitory signals. Several distinct NK-specific receptors have been identified that play an important role in the NK cell mediated recognition and killing of HLA Class I deficient target cells. Natural Cytotoxicity Receptors (NCR) refers to a class of activating receptor proteins, and the genes expressing them, that are specifically expressed in NK cells. Examples of NCRs include NKp30, NKp44, and NKp46 (see, e.g., Lanier (2001) Nat Immunol 2:23-27, Pende et al. (1999) J Exp Med. 190:1505-1516, Cantoni et al. (1999) J Exp Med. 189:787-796, Sivori et al (1997) J. Exp. Med. 186:1129-1136, Pessino et al. (1998) J Exp Med. 188(5):953-60; Mandelboim et al. (2001) Nature 409:1055-1060, the entire disclosures of which are herein incorporated by reference). These receptors are members of the Ig superfamily, and their cross-linking, induced by specific mAbs, leads to a strong NK cell activation resulting in increased intracellular Ca' levels, triggering of cytotoxicity, and lymphokine release, and an activation of NK cytotoxicity against many types of target cells.

CD94/NKG2A is an inhibitory receptor found on subsets of lymphocytes. CD94/NKG2A restricts cytokine release and cytotoxic responses of certain lymphocytes towards cells expressing the CD94/NKG2A-ligand HLA-E (see, e.g., WO99/28748). HLA-E has also been found to be secreted in soluble form by certain tumor cells (Derre et al., J Immunol 2006; 177:3100-7) and activated endothelial cells (Coupel et al., Blood 2007; 109:2806-14). Antibodies that inhibit CD94/NKG2A signalling may increase the cytokine release and cytolytic activity of lymphocytes towards HLA-E positive target cells, such as responses of CD94/NKG2A-positive NK cells towards HLA-E expressing tumor cells or virally infected cells. Therefore, therapeutic antibodies that inhibit CD94/NKG2A but that do not provoke the killing of CD94/NKG2A-expressing cells (i.e. non-depleting antibodies), may induce control of tumor-growth in cancer patients.

PD-1 is an inhibitory member of the CD28 family of receptors that also includes CD28, CTLA-4, ICOS and BTLA. PD-1 is expressed on activated B cells, T cells, and myeloid cells Okazaki et al. (2002) Curr. Opin. Immunol. 14: 391779-82; Bennett et al. (2003) J Immunol 170:711-8). Two ligands for PD-1 have been identified, PD-L1 and PD-L2, that have been shown to downregulate T cell activation upon binding to PD-1 (Freeman et al. (2000) J Exp Med 192:1027-34; Latchman et al. (2001) Nat Immunol 2:261-8; Carter et al. (2002) Eur J Immunol 32:634-43). PD-L1 is abundant in a variety of human cancers (Dong et al. (2002) Nat. Med. 8:787-9). The interaction between PD-1 and PD-L1 results in a decrease in tumor infiltrating lymphocytes, a decrease in T-cell receptor mediated proliferation, and immune evasion by the cancerous cells. Immune suppression can be reversed by inhibiting the local interaction of PD-1 with PD-L1, and the effect is additive when the interaction of PD1 with PD-L2 is blocked as well.

PD-1 blockade has resulted in impressive anti-tumor responses in numerous clinical trials. However, not all patients respond to treatment with anti-tumor responses, and furthermore some patients have cancers that relapse after treatment. Consequently, there is a need in the art for improved benefit to patients treated with inhibitors of the PD-1 axis.

SUMMARY OF THE INVENTION

The present invention provides improved methods of enhancing an anti-tumor immune response through the combined neutralization of inhibitory receptors NKG2A and PD1, e.g. via the use of antibodies. While CD8T cells and NK cells (in the periphery) do not express both NKG2A and PD-1, it has been found that tumor infiltrating lymphocytes that mediate elimination of tumor cells are capable of expressing both the inhibitory receptor PD-1 and the inhibitory receptor NKG2A. Additionally, treatment with anti-PD1 can cause upregulation of NKG2A receptors on tumor infiltrating lymphocytes, such that NKG2A may be restricting the efficacy of agents that block the PD1 axis. Since these receptors can both restrict the cytotoxic activities of tumor infiltrating lymphocytes, neutralization of the inhibitory activity of both these two receptors by antibodies enables NKG2A+PD1+ lymphocytes to effectively eliminate cancer cells. In one embodiment, the NKG2A+PD1+ lymphocytes are cytotoxic lymphocytes, optionally CD8+ T cells or NK cells.

Inhibition or neutralization the inhibitory activity of PD-1 can advantageously involve use of a polypeptide (e.g. an antibody, a polypeptide fused to an Fc domain, an immunoadhesin, etc.) that prevents PD-L1-induced PD-1 signalling, e.g. by blocking the interaction with its natural ligand PD-L1 (and optionally further blocking the interaction between PD-1 and PD-L2. In one aspect the polypeptide is an antibody that binds PD-1 (an anti-PD-1 antibody); such antibody may block the interaction between PD-1 and PD-L1 and/or between PD-1 and PD-L2. In another aspect the polypeptide is an antibody that binds PD-L1 (an anti-PD-L1 antibody) and blocks the interaction between PD-1 and PD-L1.

Accordingly, in one embodiment, provided is a method for treating or preventing a cancer in an individual, the method comprising administering to an individual: (a) a therapeutically active amount of a compound that inhibits a human NKG2A polypeptide, and (b) a therapeutically active amount of a compound that inhibits a human PD-1 polypeptide. In one embodiment, the cancer is a solid tumor. In one embodiment, the compound that inhibits a human NKG2A polypeptide is an antibody that neutralizes the inhibitory activity of NKG2A. In one embodiment, the compound that inhibits a human PD-1 polypeptide is an anti-PD-1 or anti-PDL-1 antibody that neutralizes the inhibitory activity of PD-1. The individual can be specified to be a human.

In one embodiment, provided is method of activating or potentiating the activity of a CD8+ tumor-infiltrating T cell in an individual, the method comprising administering to an individual: (a) a therapeutically active amount of a compound that inhibits a human NKG2A polypeptide, and (b) a therapeutically active amount of a compound that inhibits a human PD-1 polypeptide. In one embodiment, provided is method of activating or potentiating the activity of a tumor-infiltrating NK cell in an individual, the method comprising administering to an individual: (a) a therapeutically active amount of a compound that inhibits a human NKG2A polypeptide, and (b) a therapeutically active amount of a compound that inhibits a human PD-1 polypeptide.

In one aspect, provided is a treatment comprising administering a combination of an antibody that neutralizes the inhibitory activity of NKG2A, and antibody that neutralizes the inhibitory activity of PD-1.

In one aspect provided is a composition comprising an antibody that inhibits a human NKG2A polypeptide and an antibody that inhibits a human PD-1 polypeptide. In one aspect, the composition is for use in the treatment or prevention of a cancer, optionally a solid tumor, optionally a haematological malignancy.

In one embodiment, the anti-NKG2A antibody is administered in an amount that results in the neutralization of the inhibitory activity of human CD94/NKG2A in the human patient (in vivo), e.g., an amount that results in the neutralization of the inhibitory activity of human CD94/NKG2A on CD8 T cells and NK cells in the human patient. In one embodiment, the amount that results in the neutralization of the inhibitory activity of human CD94/NKG2A in the human patient is at least 10-fold (e.g., 10-20 fold, 10-50 fold, 10-100 fold, 20-50 fold, 20-100 fold, 30-100 fold, 50-100 fold), optionally at least 50-, 60-, 80- or 100-fold, the minimum concentration required to substantially saturate NKG2A receptors on the surface of NKG2A+ cells (e.g., in a binding assay where antibody is titrated on PBMC). In one embodiment, the anti-NKG2A antibody competes with HLA-E for binding to human NKG2A.

In one embodiment, the anti-NKG2A antibody is administered for at least one administration cycle, the administration cycle comprising at least a first and second (and optionally a $3^{rd}$, $4^{th}$, $5^{th}$, $6^{th}$, $7^{th}$ and/or $8^{th}$ or further) administration of the anti-NKG2A antibody, wherein the anti-NKG2A antibody is administered in an amount effective to achieve a continuous (minimum) blood concentration of anti-NKG2A antibody of at least 10 μg/ml (or, optionally at least 20, 30, 40 or 50 μg/mL) between the first and second (and optionally the further) administrations. Achieving or maintaining a specified continuous blood concentration means that the blood concentration does not drop substantially below the specified blood concentration for the duration of the specified time period (e.g. between two administrations of antibody, number of weeks), i.e. although the blood concentration can vary during the specified time period, the specified blood concentration represents a minimum or "trough" concentration.

In one embodiment, the anti-NKG2A antibody is administered in an amount effective to achieve a peak blood concentration of about or at least about 50, 60, 70 or 80 μg/ml, optionally at least about 100 μg/ml, upon administration (e.g. within 1 or 2 days of administration).

In one embodiment, the anti-NKG2A antibody is administered in an amount effective to achieve a continuous (minimum) blood concentration of anti-NKG2A antibody of about or at least about 10, 20, 30, 40, 50, 60, 70 or 80 μg/ml, optionally at least about 100 μg/ml, for at least one week, or at least two weeks, following administration of the antibody.

In one embodiment, the anti-NKG2A antibody is administered in an amount effective to achieve a continuous (minimum) blood concentration of anti-NKG2A antibody of about or at least about 50, 60, 70 or 80 μg/ml, optionally at least about 100 μg/ml, between two successive administrations. In one embodiment, the first and second administrations are separated in time by about two weeks, optionally about one week.

The anti-NKG2A antibody can optionally be administered in an amount effective and according to a frequency that achieves a continuous (minimum) blood concentration as specified for the entire duration of an administration cycle.

In one embodiment, the anti-NKG2A antibody is administered in combination with antibody that neutralizes a human PD-1 polypeptide, for the treatment of a solid tumor in an individual, wherein the administration cycle comprising least two administrations of the anti-NKG2A antibody, wherein the anti-NKG2A antibody in administered in an amount effective to achieve a continuous (minimum) concentration in an extravascular tissue (e.g. in the tumor environment) of at least 4 μg/mL, optionally at least 10 μg/mL between two successive administrations. Optionally, the anti-NKG2A antibody is administered in an amount effective to achieve a continuous (minimum) concentration in an extravascular tissue (e.g. in the tumor environment) of at least 4 μg/mL, optionally at least 10 μg/mL, for the entire duration of the administration cycle. In one embodiment, the anti-NKG2A antibody is administered in an amount effective to achieve a continuous (minimum) blood concentration of anti-NKG2A antibody of at least 40 μg/mL, optionally at least 100 μg/mL, between two successive administrations, or for the duration of the administration cycle.

In one embodiment, the antibody that neutralizes a human PD-1 polypeptide is administered in an amount that results in the neutralization of the inhibitory activity of human PD-1 in the human patient (in vivo), e.g. an amount that results in the neutralization of the inhibitory activity of human PD-1 on CD8 T cells and NK cells in the human patient. In one aspect, the combination is administered (or is for administration) according to a particular clinical dosage regimen, notably at a particular dose amount and according to a specific dosing schedule.

In one aspect, an antibody that neutralizes NKG2A is a non-depleting antibody, e.g. an antibody that does not kill, eliminate, lyse or induce such killing, elimination or lysis, so as to negatively affect the number of NKG2A-expressing cells present in a sample or in a subject. In one aspect an antibody that neutralizes PD-1 is a non-depleting antibody. A non-depleting antibody can, for example, lack an Fc domain or have an Fc domain with minimal or no binding to one or more Fcγ receptors (e.g. CD16). Example include antibodies with constant regions from human IgG4 isotype antibodies, antibodies of any isotype (e.g. IgG1, IgG2, IgG3) with constant regions modified to reduce or abolish binding to one or more Fcγ receptors (e.g. CD16).

In one embodiment the cancer is an advanced and/or refractory solid tumor. In one non-limiting embodiment, the cancer (e.g., the advanced refractory solid tumor) is selected from the group consisting of non-small cell lung cancer (NSCLC), kidney cancer, pancreatic or esophagus adenocarcinoma, breast cancer, renal cell carcinoma (RCC), melanoma, colorectal cancer, and ovarian cancer.

The compound that inhibits a NKG2A polypeptide (anti-NKG2A agent) is a compound that increases the ability of an NKG2A-expressing NK and/or T cells to cause the death of the HLA-E-expressing cell. Optionally, the compound that inhibits a NKG2A polypeptide is a polypeptide, optionally an antibody (e.g. monoclonal antibody), that binds a NKG2A polypeptide.

In one embodiment, the anti-NKG2A agent reduces the inhibitory activity of NKG2A by blocking binding of its ligand, HLA-E, i.e., the anti-NKG2A agent interferes with the binding of NKG2A by HLA-E. Antibody having the heavy chain of any of SEQ ID NOS: 4-8 and the light chain of SEQ ID NO: 9 is an example of such an antibody. In one embodiment, the anti-NKG2A agent reduces the inhibitory activity of NKG2A without blocking binding of its ligand, HLA-E, i.e., the anti-NKG2A agent is a non-competitive antagonist and does not interfere with the binding of NKG2A by HLA-E. The antibody having the heavy and light chain variable regions of SEQ ID NOS: 10 and 11 respectively is an example of such an antibody.

In one embodiment, the anti-NKG2A agent is antibody which binds with a significantly higher affinity to NKG2A than to one or more activating NKG2 receptors. For example, in one embodiment, the agent is antibody which binds with a significantly higher affinity to NKG2A than to NKG2C. In an additional or alternative embodiment, the agent is antibody which binds with a significantly higher affinity to NKG2A than to NKG2E. In an additional or alternative embodiment, the agent is antibody which binds with a significantly higher affinity to NKG2A than to NKG2H.

In one embodiment, the anti-NKG2A agent competes with the antibody having the heavy and light chains of SEQ ID NOS: 4-8 and 9 respectively, or the antibody having the heavy and light chain variable regions of SEQ ID NOS: 10 and 11 respectively, in binding to CD94/NKG2A. The agent can be, e.g., a human or humanized anti-NKG2A antibody.

In one embodiment, the anti-NKG2A antibody is a humanized antibody having the heavy chain CDRs of any of the heavy chains of any of SEQ ID NOS: 4-8 and the light chain CDRs of the light chain of SEQ ID NO: 9 respectively. In one embodiment, the anti-NKG2A antibody is a humanized antibody having the heavy chain variable region of any of the heavy chains of any of SEQ ID NOS: 4-8 and the light chain variable region of the light chain of SEQ ID NO: 9 respectively. Exemplary complementarity-determining region (CDR) residues or sequences and/or sites for amino acid substitutions in framework region (FR) of such humanized antibodies having improved properties such as, e.g., lower immunogenicity, improved antigen-binding or other functional properties, and/or improved physicochemical properties such as, e.g., better stability, are provided.

In certain optional aspects, patients can be identified for treatment with an anti-NKG2A agent and PD1-neutralizing agent by assessing the presence in a tumor sample (e.g. tumor tissue and/or tumor adjacent tissue) of ligands for NKG2A, optionally further a ligand of PD-1. In one embodiment of any of the therapeutic uses or cancer treatment or prevention methods herein, the treatment or prevention of a cancer in an individual comprises:

a) determining the HLA-E polypeptide status of malignant cells within the individual having a cancer, and b) upon a determination that HLA-E polypeptides are prominently expressed by (e.g. on the surface of) malignant cells (e.g. tumor cells), administering to the individual a compound that neutralizes the inhibitory activity of a human NKG2A polypeptide and an agent that inhibits a human PD-1 polypeptide.

In one embodiment of any of the therapeutic uses or cancer treatment or prevention methods herein, the treatment or prevention of a cancer in an individual comprises:

a) determining the HLA-E polypeptide status and PD-L1 polypeptide status of malignant cells (e.g. tumor cells) within the individual having a cancer, and b) upon a determination that HLA-E and PD-L1 polypeptides are prominently expressed on the surface of malignant cells, administering to the individual a compound that neutralizes the inhibitory activity of a human NKG2A polypeptide and an agent that inhibits a human PD-1 polypeptide.

In one embodiment, a determination that a biological sample (e.g., a sample comprising tumor cells, tumor tissue and/or tumor adjacent tissue) prominently expresses HLA-E nucleic acid or polypeptide indicates that the individual has a cancer that can be treated with an agent that inhibits NKG2A in combination with an agent that inhibits a human PD-1 polypeptide.

In one embodiment of any of the methods, determining the HLA-E polypeptide status or determining the level of expression in step (a) comprises determining the level of expression of a HLA-E nucleic acid or polypeptide of malignant cells in a biological sample and comparing the level to a reference level (e.g. a value, weak or strong cell surface staining, etc.). The reference level may, for example, correspond to a healthy individual, to an individual deriving no/low clinical benefit from treatment with an anti-NKG2A antibody (optionally in combination with an agent that inhibits a human PD-1 polypeptide), or to an individual deriving substantial clinical benefit from treatment with an anti-NKG2A antibody (optionally in combination with an agent that inhibits a human PD-1 polypeptide). A determination that a biological sample expresses HLA-E nucleic acid or polypeptide at a level that is increased (e.g. a high value, strong surface staining, a level that corresponds to that of an individual deriving substantial clinical benefit from treatment with an anti-NKG2A antibody, a level that is higher than that corresponding to an individual deriving no/low clinical benefit from treatment with an anti-NKG2A antibody, etc.) indicates that the individual has a cancer that can be treated with an anti-NKG2A antibody in combination with an agent that inhibits a human PD-1 polypeptide, e.g. according to the treatment methods described herein.

In one embodiment provided is a method for identifying NKG2A-inhibited PD-1-expressing lymphocytes, the method comprising:

a) determining the NKG2A and PD-1 polypeptide status of NK and/or CD8 T lymphocytes in a biological sample, and b) wherein a determination that NKG2A and PD-1 polypeptides are expressed on the surface of a significant proportion of the lymphocytes, indicates that the lymphocytes are NKG2A-inhibited PD-1-expressing lymphocytes. Optionally the lymphocytes are tumor infiltrating lymphocytes. Optionally the biological sample is a sample that comprises tumor tissue and/or tumor adjacent tissue.

In one embodiment provided is a method for identifying an individual having a cancer for whom treatment with an anti-NKG2A agent is suitable, the method comprising:

a) determining the NKG2A and PD-1 polypeptide status of tumor infiltrating lymphocytes from the individual, and b) wherein a determination that NKG2A and PD-1 polypeptides are expressed on the surface of a significant proportion of tumor infiltrating lymphocytes from the individual, optionally TILs of a pre-defined subset (e.g. CD8 T cells, NK cells), indicates that treatment with a compound that neutralizes the inhibitory activity of a human NKG2A polypeptide and an agent that inhibits a human PD-1 polypeptide is suitable for the individual.

In one embodiment provided is a method for treatment or prevention of a cancer in an individual comprises:

a) determining the NKG2A and PD-1 polypeptide status of tumor infiltrating lymphocytes from the individual, and b) upon a determination that NKG2A and PD-1 polypeptides are expressed on the surface of a significant proportion of tumor infiltrating lymphocytes, optionally TILs of a pre-defined subset (e.g. CD8 T cells, NK cells), from the individual, administering to the individual a therapeutic regimen that comprises a compound that neutralizes the inhibitory activity of a human NKG2A polypeptide and an agent that inhibits a human PD-1 polypeptide.

In one embodiment, the tumor infiltrating lymphocytes are CD8 T cells. In one embodiment, the tumor infiltrating lymphocytes are NK cells. In one embodiment, at least 10, 15, 20, 25% of CD8 T cells are NKG2A$^+$PD$^+$. In one embodiment, at least 10%, 15%, 20% or 25% of CD8 T cells are NKG2A$^+$PD-1$^+$. In one embodiment, at least 20%, 25%, 30% or 35% of NK cells are NKG2A$^+$PD-1$^+$.

In other embodiments, pharmaceutical compositions and kits are provided, as well as methods for using them. In one embodiment, provided is a pharmaceutical composition comprising a compound that neutralizes the inhibitory activity of a human NKG2A polypeptide and an agent that inhibits a human PD-1 polypeptide. In one embodiment, provided is a kit comprising a compound that neutralizes the inhibitory activity of a human NKG2A polypeptide and an agent that inhibits a human PD-1 polypeptide.

These aspects are more fully described in, and additional aspects, features, and advantages will be apparent from, the description of the invention provided herein.

BRIEF DESCRIPTION OF THE DRAWINGS

FIGS. 3A and 3B show NKG2A and PD-1 expression in tumor bearing mice. RMA Rae1 (top row), MC38 (medium row) and RMA (bottom row) tumor bearing mice were sacrificed when their tumors reached respectively the volumes of 500, 2000 and 800 mm³. NK cells (FIG. 3A) and CD8 T cells (FIG. 3B) were analyzed by flow cytometry in spleen, tumor draining lymph node (LN) and tumor for NKG2A/C/E and PD-1 expression.

DETAILED DESCRIPTION

Definitions

Figure 1A:
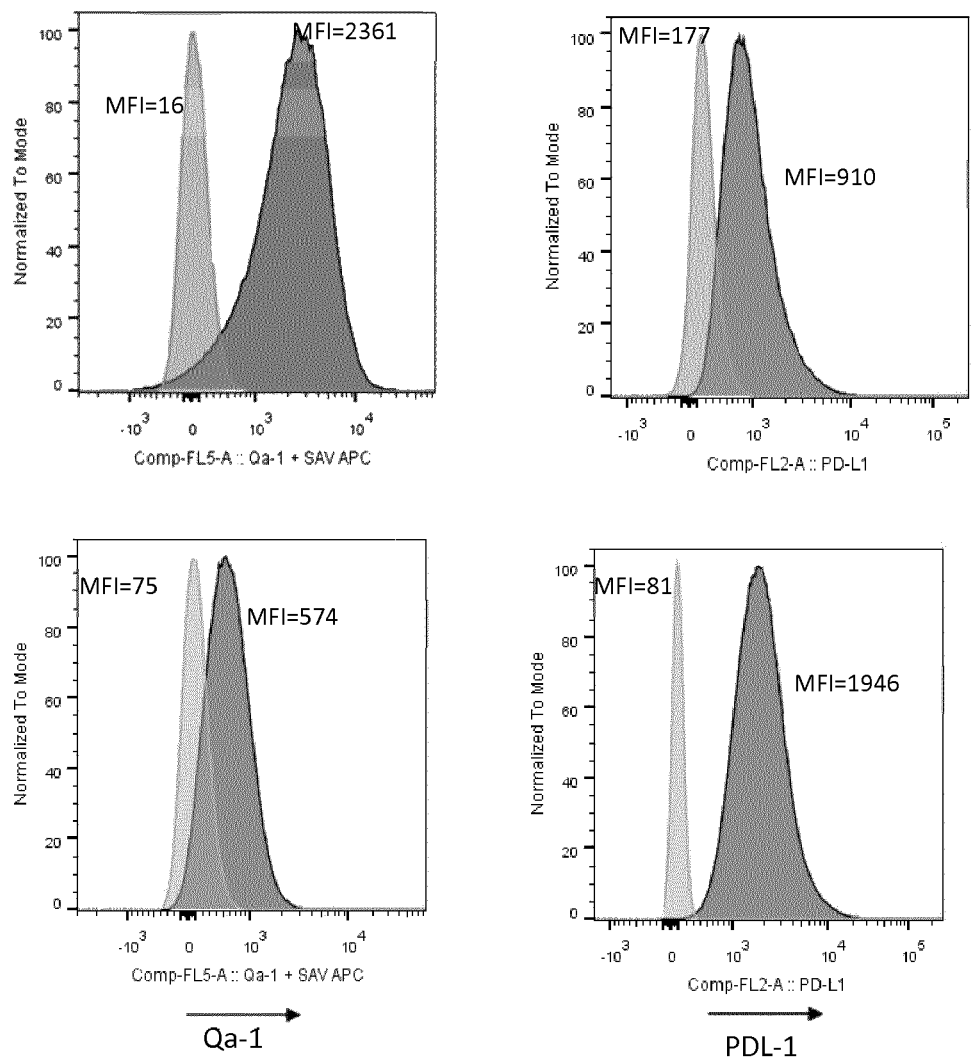
FIGS. 1A and 1B shows PD-L1+Qa-1+ RMA-S Qa-1 Qdm B2m and A20 tumor cells are infiltrated by NK cells expressing NKG2A and CD8 T cells expressing NKG2A and/or PD-1.RMA-S Qa-1 Qdm B2m (top row) and A20 (bottom row) tumor bearing mice were sacrificed when tumor volumes were around 500 mm³. Tumor cells (FIG. 1A) and tumor infiltrating lymphocytes-TIL- (FIG. 1B) were analyzed by flow cytometry respectively for the expression of Qa-1 and PDL-1 for tumor cells and NKG2A/C/E and PD-1 for TIL. MFI:Median of fluorescence intensity.

As used in the specification, "a" or "an" may mean one or more. As used in the claim(s), when used in conjunction with the word "comprising", the words "a" or "an" may mean one or more than one. As used herein "another" may mean at least a second or more.

Where "comprising" is used, this can optionally be replaced by "consisting essentially of" or by "consisting of".

NKG2A (OMIM 161555, the entire disclosure of which is herein incorporated by reference) is a member of the NKG2 group of transcripts (Houchins, et al. (1991) J. Exp. Med. 173:1017-1020). NKG2A is encoded by 7 exons spanning 25 kb, showing some differential splicing. Together with CD94, NKG2A forms the heterodimeric inhibitory receptor CD94/NKG2A, found on the surface of subsets of NK cells, α/β T cells, γ/δ T cells, and NKT cells. Similar to inhibitory KIR receptors, it possesses an ITIM in its cytoplasmic domain. As used herein, "NKG2A" refers to any variant, derivative, or isoform of the NKG2A gene or encoded protein. Human NKG2A comprises 233 amino acids in 3 domains, with a cytoplasmic domain comprising residues 1-70, a transmembrane region comprising residues 71-93, and an extracellular region comprising residues 94-233, of the following sequence:

```
                                        (SEQ ID NO: 1)
MDNQGVIYSDLNLPPNPKRQQRKPKGNKSSILATEQEITYAELNLQKA

SQDFQGNDKTYHCKDLPSAPEKLIVGILGIICLILMASVVTIVVIPST

LIQRHNNSSLNTRTQKARHCGHCPEEWITYSNSCYYIGKERRTWEESL

LACTSKNSSLLSIDNEEEMKFLSIISPSSWIGVFRNSSHHPWVTMNGL

AFKHEIKDSDNAELNCAVLQVNRLKSAQCGSSIIYHCKHKL.
```

NKG2C (OMIM 602891, the entire disclosure of which is herein incorporated by reference) and NKG2E (OMIM 602892, the entire disclosure of which is herein incorporated by reference) are two other members of the NKG2 group of transcripts (Gilenke, et al. (1998) Immunogenetics 48:163-173). The CD94/NKG2C and CD94/NKG2E receptors are activating receptors found on the surface of subsets of lymphocytes such as NK cells and T-cells.

HLA-E (OMIM 143010, the entire disclosure of which is herein incorporated by reference) is a nonclassical MHC molecule that is expressed on the cell surface and regulated by the binding of peptides, e.g., such as fragments derived from the signal sequence of other MHC class I molecules. Soluble versions of HLA-E have also been identified. In addition to its T-cell receptor binding properties, HLA-E binds subsets of natural killer (NK) cells, natural killer T-cells (NKT) and T cells (α/β and γ/δ), by binding specifically to CD94/NKG2A, CD94/NKG2B, and CD94/NKG2C (see, e.g., Braud et al. (1998) Nature 391:795-799, the entire disclosure of which is herein incorporated by reference). Surface expression of HLA-E protects target cells from lysis by CD94/NKG2A+ NK, T, or NKT cell clones. As used herein, "HLA-E" refers to any variant, derivative, or isoform of the HLA-E gene or encoded protein.

In the context of the present invention, "NKG2A" or "CD94/NKG2A positive lymphocyte" refers to cells of the lymphoid lineage (e.g. NK-, NKT- and T-cells) expressing CD94/NKG2A on the cell-surface, which can be detected by e.g. flow-cytometry using antibodies that specifically recognize a combined epitope on CD94 and NKG2A or and epitope on NKG2A alone. "NKG2A positive lymphocyte" also includes immortal cell lines of lymphoid origin (e.g. NKL, NK-92).

In the context of the present invention, "reduces the inhibitory activity of NKG2A", "neutralizes NKG2A" or "neutralizes the inhibitory activity of NKG2A" refers to a process in which CD94/NKG2A is inhibited in its capacity to negatively affect intracellular processes leading to lymphocyte responses such as cytokine release and cytotoxic responses. This can be measured for example in a NK- or T-cell based cytotoxicity assay, in which the capacity of a therapeutic compound to stimulate killing of HLA-E positive cells by CD94/NKG2A positive lymphocytes is measured. In one embodiment, an antibody preparation causes at least a 10% augmentation in the cytotoxicity of a CD94/NKG2A-restricted lymphocyte, optionally at least a 40% or 50% augmentation in lymphocyte cytotoxicity, optionally at least a 70% augmentation in NK cytotoxicity", and referring to the cytotoxicity assays described. If an anti-NKG2A antibody reduces or blocks CD94/NKG2A interactions with HLA-E, it may increase the cytotoxicity of CD94/NKG2A-restricted lymphocytes. This can be evaluated, for example, in a standard 4-hour in vitro cytotoxicity assay using, e.g., NK cells that express CD94/NKG2A, and target cells that express HLA-E. Such NK cells do not efficiently kill targets that express HLA-E because CD94/NKG2A recognizes HLA-E, leading to initiation and propagation of inhibitory signaling that prevents lymphocyte-mediated cytolysis. Such an in vitro cytotoxicity assay can be carried out by standard methods that are well known in the art, as described for example in Coligan et al., eds., Current Protocols in Immunology, Greene Publishing Assoc. and Wiley Interscience, N.Y., (1992, 1993). Chromium release and/or other parameters to assess the ability of the antibody to stimulate lymphocytes to kill target cells such as P815, K562 cells, or appropriate tumor cells are also disclosed in Sivori et al., J. Exp. Med. 1997; 186:1129-1136; Vitale et al., J. Exp. Med. 1998; 187:2065-2072; Pessino et al. J. Exp. Med. 1998; 188:953-960; Neri et al. Clin. Diag. Lab. Immun. 2001; 8:1131-1135; Pende et al. J. Exp. Med. 1999; 190:1505-1516, the entire disclosures of each of which are herein incorporated by reference. The target cells are labeled with $^{51}$Cr prior to addition of NK cells, and then the killing is estimated as proportional to the release of $^{51}$Cr from the cells to the medium, as a result of killing. The addition of an antibody that prevents CD94/NKG2A from binding to HLA-E results in prevention of the initiation and propagation of inhibitory signaling via CD94/NKG2A. Therefore, addition of such agents results in increases in lymphocyte-mediated killing of the target cells. This step thereby identifies agents that prevent CD94/NKG2A-induced negative signaling by, e.g., blocking ligand binding. In a particular $^{51}$Cr-release cytotoxicity assay, CD94/NKG2A-expressing NK effector-cells can kill HLA-E-negative LCL 721.221 target cells, but less well HLA-E-expressing LCL 721.221-Cw3 control cells. In contrast, YTS effector-cells that lack CD94/NKG2A kill both cell-lines efficiently. Thus, NK effector cells kill less efficiently HLA-E$^+$ LCL 721.221-Cw3 cells due to HLA-E-induced inhibitory signaling via CD94/NKG2A. When NK cells are pre-incubated with blocking anti-CD94/NKG2A antibodies according to the present invention in such a $^{51}$Cr-release cytotoxicity assay, HLA-E-expressing LCL 721.221-Cw3 cells are more efficiently killed, in an antibody-concentration-dependent fashion. The inhibitory activity (i.e. cytotoxicity enhancing potential) of an anti-NKG2A antibody can also be assessed in any of a number of other ways, e.g., by its effect on intracellular free calcium as described, e.g., in Sivori et al., J. Exp. Med. 1997; 186:1129-1136, the disclosure of which is herein incorporated by reference. Activation of NK cell cytotoxicity can be assessed for example by measuring an increase in cytokine production (e.g. IFN-γ production) or cytotoxicity markers (e.g. CD107 or CD137 mobilization). In an exemplary protocol, IFN-γ production from PBMC is assessed by cell surface and intracytoplasmic staining and analysis by flow cytometry after 4 days in culture. Briefly, Brefeldin A (Sigma Aldrich) is added at a final concentration of 5 µg/ml for the last 4 hours of culture. The cells are then incubated with anti-CD3 and anti-CD56 mAb prior to permeabilization (IntraPrep™; Beckman Coulter) and staining with PE-anti-IFN-γ or PE-IgG1 (Pharmingen). GM-CSF and IFN-γ production from polyclonal activated NK cells are measured in supernatants using ELISA (GM-CSF: DuoSet Elisa, R&D Systems, Minneapolis, Minn., IFN-γ: OptEIA set, Pharmingen).

As used herein, the terms "PD-1" refers to the protein Programmed Death 1 (PD-1) (also referred to as "Programmed Cell Death 1"), an inhibitory member of the CD28 family of receptors, that also includes CD28, CTLA-4, ICOS and BTLA. The complete human PD-1 sequence can be found under GenBank Accession No. U64863, shown as follows:

(SEQ ID NO: 2)
MQIPQAPWPVVWAVLQLGWRPGWFLDSPDRPWNPPTFFPALLVVTEGD

NATFTCSFSNTSESFVLNWYRMSPSNQTDKLAAFPEDRSQPGQDCRFR

VTQLPNGRDFHMSVVRARRNDSGTYLCGAISLAPKAQIKESLRAELRV

TERRAEVPTAHPSPSPRPAGQFQTLVVGVVGGLLGSLVLLVWVLAVIC

-continued

SRAARGTIGARRTGQPLKEDPSAVPVFSVDYGELDFQWREKTPEPPVP

CVPEQTEYATIVFPSGMGTSSPARRGSADGPRSAQPLRPEDGHCSWPL.

"PD-1" also includes any variant, derivative, or isoform of the PD-1 gene or encoded protein. PD-1 is expressed on activated B cells, T cells, and myeloid cells Okazaki et al. (2002) Curr. Opin. Immunol. 14: 391779-82; Bennett et al. (2003) J Immunol 170:711-8). The initial members of the family, CD28 and ICOS, were discovered by functional effects on augmenting T cell proliferation following the addition of monoclonal antibodies (Hutloff et al. (1999) Nature 397:263-266; Hansen et al. (1980) Immunogenics 10:247-260). Two ligands for PD-1 have been identified, PD-L1 and PD-L2, that have been shown to downregulate T cell activation upon binding to PD-1 (Freeman et al. (2000) J Exp Med 192:1027-34; Latchman et al. (2001) Nat Immunol 2:261-8; Carter et al. (2002) Eur J Immunol 32:634-43). Both PD-L1 and PD-L2 are B7 homologs that bind to PD-1, but do not bind to other CD28 family members.

The complete human PD-L1 sequence can be found under UniProtKB/Swiss-Prot, identifier Q9NZQ7-1, shown as follows:

```
                                              (SEQ ID NO: 3)
MRIFAVFIFM  TYWHLLNAFT  VTVPKDLYVV  EYGSNMTIEC

KFPVEKQLDL  AALIVYWEME  DKNIIQFVHG  EEDLKVQHSS

YRQRARLLKD  QLSLGNAALQ  ITDVKLQDAG  VYRCMISYGG

ADYKRITVKV  NAPYNKINQR  ILVVDPVTSE  HELTCQAEGY

PKAEVIWTSS  DHQVLSGKTT  TTNSKREEKL  FNVTSTLRIN

TTTNEIFYCT  FRRLDPEENH  TAELVIPELP  LAHPPNERTH

LVILGAILLC  LGVALTFIFR  LRKGRMMDVK  KCGIQDTNSK

KQSDTHLEET.
```

PD-L1 is abundant in a variety of human cancers (Dong et al. (2002) Nat. Med. 8:787-9). The interaction between PD-1 and PD-L1 results in a decrease in tumor infiltrating lymphocytes, a decrease in T-cell receptor mediated proliferation, and immune evasion by the cancerous cells (Dong et al. (2003) J. Mol. Med. 81:281-7; Blank et al. (2005) Cancer Immunol. Immunother. 54:307-314; Konishi et al. (2004) Clin. Cancer Res. 10:5094-100). Immune suppression can be reversed by inhibiting the local interaction of PD-1 with PD-L1, and the effect is additive when the interaction of PD-1 with PD-L2 is blocked as well.

In the context of the present invention, "reduces the inhibitory activity of human PD1", "neutralizes PD-1" or "neutralizes the inhibitory activity of human PD-1" refers to a process in which PD-1 is inhibited in its signal transduction capacity resulting from the interaction of PD-1 with one or more of its binding partners, such as PD-L1 or PD-L2. An agent that neutralizes the inhibitory activity of PD-1 decreases, blocks, inhibits, abrogates or interferes with signal transduction resulting from the interaction of PD-1 with one or more of its binding partners, such as PD-L1, PD-L2. Such an agent can thereby reduce the negative costimulatory signal mediated by or through cell surface proteins expressed on T lymphocytes, so as to enhance T-cell effector functions such as proliferation, cytokine production and/or cytotoxicity.

Whenever within this whole specification "treatment of cancer" or the like is mentioned with reference to anti-NKG2A and anti-PD-1 or anti-PD-L1 binding agent (e.g. antibody), are comprised: (a) method of treatment of cancer, said method comprising the step of administering (for at least one treatment) an NKG2A and anti-PD-1 or anti-PD-L1 binding agent, (e.g., together or each separately in a pharmaceutically acceptable carrier material) to an individual, a mammal, especially a human, in need of such treatment, in a dose that allows for the treatment of cancer, (a therapeutically effective amount), optionally in a dose (amount) as specified herein; (b) the use of an anti-NKG2A and anti-PD-1 or anti-PD-L1 binding agent for the treatment of cancer, or an anti-NKG2A binding agent, for use in said treatment (especially in a human); (c) the use of an anti-NKG2A and anti-PD-1 or anti-PD-L1 binding agent for the manufacture of a pharmaceutical preparation for the treatment of cancer, a method of using an anti-NKG2A and anti-PD-1 or anti-PD-L1 binding agent for the manufacture of a pharmaceutical preparation for the treatment of cancer, comprising admixing an anti-NKG2A and anti-PD-1 or anti-PD-L1 binding agent with a pharmaceutically acceptable carrier, or a pharmaceutical preparation comprising an effective dose of an anti-NKG2A and anti-PD-1 or anti-PD-L1 binding agent that is appropriate for the treatment of cancer; or (d) any combination of a), b), and c), in accordance with the subject matter allowable for patenting in a country where this application is filed.

The term "biopsy" as used herein is defined as removal of a tissue for the purpose of examination, such as to establish diagnosis. Examples of types of biopsies include by application of suction, such as through a needle attached to a syringe; by instrumental removal of a fragment of tissue; by removal with appropriate instruments through an endoscope; by surgical excision, such as of the whole lesion; and the like.

The term "antibody," as used herein, refers to polyclonal and monoclonal antibodies. Depending on the type of constant domain in the heavy chains, antibodies are assigned to one of five major classes: IgA, IgD, IgE, IgG, and IgM. Several of these are further divided into subclasses or isotypes, such as IgG1, IgG2, IgG3, IgG4, and the like. An exemplary immunoglobulin (antibody) structural unit comprises a tetramer. Each tetramer is composed of two identical pairs of polypeptide chains, each pair having one "light" (about 25 kDa) and one "heavy" chain (about 50-70 kDa). The N-terminus of each chain defines a variable region of about 100 to 110 or more amino acids that is primarily responsible for antigen recognition. The terms variable light chain ($V_L$) and variable heavy chain ($V_H$) refer to these light and heavy chains respectively. The heavy-chain constant domains that correspond to the different classes of immunoglobulins are termed "alpha," "delta," "epsilon," "gamma" and "mu," respectively. The subunit structures and three-dimensional configurations of different classes of immunoglobulins are well known. IgG are the exemplary classes of antibodies employed herein because they are the most common antibodies in the physiological situation and because they are most easily made in a laboratory setting. Optionally the antibody is a monoclonal antibody. Particular examples of antibodies are humanized, chimeric, human, or otherwise-human-suitable antibodies. "Antibodies" also includes any fragment or derivative of any of the herein described antibodies.

The term "specifically binds to" means that an antibody can bind preferably in a competitive binding assay to the binding partner, e.g. NKG2A, PD-1, PD-L1, as assessed using either recombinant forms of the proteins, epitopes therein, or native proteins present on the surface of isolated target cells. Competitive binding assays and other methods for determining specific binding are well known in the art. For example binding can be detected via radiolabels, physical methods such as mass spectrometry, or direct or indirect fluorescent labels detected using, e.g., cytofluorometric analysis (e.g. FACScan). Binding above the amount seen with a control, non-specific agent indicates that the agent binds to the target. An agent that specifically binds NKG2A may bind NKG2A alone or NKG2A as a dimer with CD94.

When an antibody is said to "compete with" a particular monoclonal antibody, it means that the antibody competes with the monoclonal antibody in a binding assay using either recombinant molecules (e.g., NKG2A, PD-1, PD-L1) or surface expressed molecules (e.g., NKG2A, PD-1, PD-L1). For example, if a test antibody reduces the binding of an antibody having a heavy chain of any of SEQ ID NO: 4-8 and a light chain of SEQ ID NO: 9 to a NKG2A polypeptide or NKG2A-expressing cell in a binding assay, the antibody is said to "compete" respectively with such antibody.

The term "affinity", as used herein, means the strength of the binding of an antibody to an epitope. The affinity of an antibody is given by the dissociation constant Kd, defined as $[Ab] \times [Ag]/[Ab-Ag]$, where [Ab-Ag] is the molar concentration of the antibody-antigen complex, [Ab] is the molar concentration of the unbound antibody and [Ag] is the molar concentration of the unbound antigen. The affinity constant $K_a$ is defined by 1/Kd. Methods for determining the affinity of mAbs can be found in Harlow, et al., Antibodies: A Laboratory Manual, Cold Spring Harbor Laboratory Press, Cold Spring Harbor, N.Y., 1988), Coligan et al., eds., Current Protocols in Immunology, Greene Publishing Assoc. and Wiley Interscience, N.Y., (1992, 1993), and Muller, Meth. Enzymol. 92:589-601 (1983), which references are entirely incorporated herein by reference. One standard method well known in the art for determining the affinity of mAbs is the use of surface plasmon resonance (SPR) screening (such as by analysis with a BIAcore™ SPR analytical device).

Within the context herein a "determinant" designates a site of interaction or binding on a polypeptide.

The term "epitope" refers to an antigenic determinant, and is the area or region on an antigen to which an antibody binds. A protein epitope may comprise amino acid residues directly involved in the binding as well as amino acid residues which are effectively blocked by the specific antigen binding antibody or peptide, i.e., amino acid residues within the "footprint" of the antibody. It is the simplest form or smallest structural area on a complex antigen molecule that can combine with e.g., an antibody or a receptor. Epitopes can be linear or conformational/structural. The term "linear epitope" is defined as an epitope composed of amino acid residues that are contiguous on the linear sequence of amino acids (primary structure). The term "conformational or structural epitope" is defined as an epitope composed of amino acid residues that are not all contiguous and thus represent separated parts of the linear sequence of amino acids that are brought into proximity to one another by folding of the molecule (secondary, tertiary and/or quaternary structures). A conformational epitope is dependent on the 3-dimensional structure. The term 'conformational' is therefore often used interchangeably with 'structural'.

The term "agent" is used herein to denote a chemical compound, a mixture of chemical compounds, a biological macromolecule, or an extract made from biological materials. The term "therapeutic agent" refers to an agent that has biological activity.

For the purposes herein, a "humanized" or "human" antibody refers to an antibody in which the constant and variable framework region of one or more human immunoglobulins is fused with the binding region, e.g. the CDR, of an animal immunoglobulin. Such antibodies are designed to maintain the binding specificity of the non-human antibody from which the binding regions are derived, but to avoid an immune reaction against the non-human antibody. Such antibodies can be obtained from transgenic mice or other animals that have been "engineered" to produce specific human antibodies in response to antigenic challenge (see, e.g., Green et al. (1994) Nature Genet 7:13; Lonberg et al. (1994) Nature 368:856; Taylor et al. (1994) Int Immun 6:579, the entire teachings of which are herein incorporated by reference). A fully human antibody also can be constructed by genetic or chromosomal transfection methods, as well as phage display technology, all of which are known in the art (see, e.g., McCafferty et al. (1990) Nature 348:552-553). Human antibodies may also be generated by in vitro activated B cells (see, e.g., U.S. Pat. Nos. 5,567,610 and 5,229,275, which are incorporated in their entirety by reference).

A "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity.

The terms "Fc domain," "Fc portion," and "Fc region" refer to a C-terminal fragment of an antibody heavy chain, e.g., from about amino acid (aa) 230 to about aa 450 of human γ (gamma) heavy chain or its counterpart sequence in other types of antibody heavy chains (e.g., α, δ, ε and μ for human antibodies), or a naturally occurring allotype thereof. Unless otherwise specified, the commonly accepted Kabat amino acid numbering for immunoglobulins is used throughout this disclosure (see Kabat et al. (1991) Sequences of Protein of Immunological Interest, 5th ed., United States Public Health Service, National Institute of Health, Bethesda, Md.).

The terms "isolated", "purified" or "biologically pure" refer to material that is substantially or essentially free from components which normally accompany it as found in its native state. Purity and homogeneity are typically determined using analytical chemistry techniques such as polyacrylamide gel electrophoresis or high performance liquid chromatography. A protein that is the predominant species present in a preparation is substantially purified.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (nonrecombinant) form of the cell or express native genes that are otherwise abnormally expressed, under expressed or not expressed at all.

Within the context herein, the term antibody that "binds" a polypeptide or epitope designates an antibody that binds said determinant with specificity and/or affinity.

The term "identity" or "identical", when used in a relationship between the sequences of two or more polypeptides, refers to the degree of sequence relatedness between polypeptides, as determined by the number of matches between strings of two or more amino acid residues. "Identity" measures the percent of identical matches between the smaller of two or more sequences with gap alignments (if any) addressed by a particular mathematical model or computer program (i.e., "algorithms"). Identity of related polypeptides can be readily calculated by known methods. Such methods include, but are not limited to, those described in Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987; Sequence Analysis Primer, Gribskov, M. and Devereux, J., eds., M. Stockton Press, New York, 1991; and Carillo et al., SIAM J. Applied Math. 48, 1073 (1988).

Methods for determining identity are designed to give the largest match between the sequences tested. Methods of determining identity are described in publicly available computer programs. Computer program methods for determining identity between two sequences include the GCG program package, including GAP (Devereux et al., Nucl. Acid. Res. 12, 387 (1984); Genetics Computer Group, University of Wisconsin, Madison, Wis.), BLASTP, BLASTN, and FASTA (Altschul et al., J. Mol. Biol. 215, 403-410 (1990)). The BLASTX program is publicly available from the National Center for Biotechnology Information (NCBI) and other sources (BLAST Manual, Altschul et al. NCB/NLM/NIH Bethesda, Md. 20894; Altschul et al., supra). The well-known Smith Waterman algorithm may also be used to determine identity.

NKG2A-Neutralizing Therapeutic Agents

The anti-NKG2A agent binds an extra-cellular portion of human CD94/NKG2A receptor and reduces the inhibitory activity of human CD94/NKG2A receptor expressed on the surface of a CD94/NKG2A positive lymphocyte. In one embodiment the agent competes with HLA-E in binding to CD94/NKG2A, i.e. the agent blocks the interaction between CD94/NKG2A and its ligand HLA-E. In another embodiment the agent does not compete with HLA-E in binding to CD94/NKG2A; i.e. the agent is capable of binding CD94/NKG2A simultaneously with HLA-E. The antibody may bind a combined epitope on CD94 and NKG2A or and epitope on NKG2A alone.

In one aspect the anti-NKG2A agent is an antibody selected from a fully human antibody, a humanized antibody, and a chimeric antibody. In one aspect, the agent comprises a constant domain derived from a human IgG1, IgG2, IgG3 or IgG4 antibody. In one aspect, the agent is a fragment of an antibody selected from IgA, an IgD, an IgG, an IgE and an IgM antibody. In one aspect, the agent is an antibody fragment selected from a Fab fragment, a Fab' fragment, a Fab'-SH fragment, a F(ab)2 fragment, a F(ab')2 fragment, an Fv fragment, a Heavy chain Ig (a llama or camel Ig), a $V_{HH}$ fragment, a single domain FV, and a single-chain antibody fragment. In one aspect, the agent is a synthetic or semisynthetic antibody-derived molecule selected from a scFV, a dsFV, a minibody, a diabody, a triabody, a kappa body, an IgNAR; and a multispecific antibody.

Optionally, the anti-NKG2A antibodies do not demonstrate substantial specific binding to Fcγ receptors, e.g. CD16. Such antibodies may comprise constant regions of various heavy chains that are known not to bind Fc receptors. One such example is a human IgG4 constant region. In one embodiment, the IgG4 antibody comprises a modification to prevent the formation of half antibodies (fab arm exchange) in vivo, e.g., the antibody comprises an IgG4 heavy chain comprising a serine to proline mutation in residue 241, corresponding to position 228 according to the EU-index (Kabat et al., "Sequences of proteins of immunological interest", 5$^{th}$ ed., NIH, Bethesda, M L, 1991). Such modified IgG4 antibodies will remain intact in vivo and maintain a bivalent (high affinity) binding to NKG2A, as opposed to native IgG4 that will undergo fab arm exchange in vivo such that they bind to NKG2A in monovalent manner which can alter binding affinity. Alternatively, antibody fragments that do not comprise constant regions, such as Fab or F(ab')2 fragments, can be used to avoid Fc receptor binding. Fc receptor binding can be assessed according to methods known in the art, including for example testing binding of an antibody to Fc receptor protein in a BIACORE assay. Also, any human antibody type (e.g. IgG1, IgG2, IgG3 or IgG4) can be used in which the Fc portion is modified to minimize or eliminate binding to Fc receptors (see, e.g., WO03101485, the disclosure of which is herein incorporated by reference). Assays such as, e.g., cell based assays, to assess Fc receptor binding are well known in the art, and are described in, e.g., WO03101485.

The present invention thus concerns antibodies or other agents binding to NKG2A. In one aspect, the antibody binds to NKG2A with a KD at least 100-fold lower than to human NKG2C and/or NKG2E.

In one aspect of the invention, the agent reduces CD94/NKG2A-mediated inhibition of a CD94/NKG2A-expressing lymphocyte by interfering with CD94/NKG2A signalling by, e.g., interfering with the binding of HLA-E by NKG2A, preventing or inducing conformational changes in the CD94/NKG2A receptor, and/or affecting dimerization and/or clustering of the CD94/NKG2A receptor.

In one aspect of the invention, the agent binds to an extracellular portion of NKG2A with a KD at least 100 fold lower than to NKG2C. In a further preferred aspect, the agent binds to an extracellular portion of NKG2A with a KD at least 150, 200, 300, 400, or 10,000 fold lower than to NKG2C. In another aspect of the invention, the agent binds to an extracellular portion of NKG2A with a KD at least 100 fold lower than to NKG2C, NKG2E and/or NKG2H molecules. In a further preferred aspect, the agent binds to an extracellular portion of NKG2A with a KD at least 150, 200, 300, 400, or 10,000 fold lower than to NKG2C, NKG2C and/or NKG2H molecules. This can be measured, for instance, in BiaCore experiments, in which the capacity of agents to bind the extracellular portion of immobilized CD94/NKG2A (e.g. purified from CD94/NKG2 expressing cells, or produced in a bio-system) is measured and compared to the binding of agents to similarly produced CD94/NKG2C and/or other CD94/NKG2 variants in the same assay. Alternatively, the binding of agents to cells that either naturally express, or over-express (e.g. after transient or stable transfection), CD94/NKG2A can be measured and compared to binding of cells expressing CD94/NKG2C and/or other CD94/NKG2 variants. Anti-NKG2A antibodies may optionally bind NKG2B, which is an NKG2A splice variant forming an inhibitory receptor together with CD94. In one embodiment, affinity can be measured using the methods disclosed in U.S. Pat. No. 8,206,709, for example by assessing binding to covalently immobilized NKG2A-CD94-Fc fusion protein by Biacore as shown in Example 8 of U.S. Pat. No. 8,206,709, the disclosure of which is incorporate herein by reference.

The anti-NKG2A antibody can be a humanized antibody, for example comprising a VH human acceptor framework from a human acceptor sequence selected from, e.g., VH1_18, VH5_a, VH5_51, VH1_f, and VH1_46, and a JH6 J-segment, or other human germline VH framework sequences known in the art. The VL region human acceptor sequence may be, e.g., VKI_O2/JK4.

In one embodiment, the antibody is a humanized antibody based on antibody Z270. Different humanized Z270VH chains are shown in SEQ ID NOS: 4-8 (variable region domain amino acid underlined). HumZ270VH6 (SEQ ID NO: 4) is based on VH5_51; HumZ270VH1 (SEQ ID NO: 5) is based on VH1_18; humZ270VH5 (SEQ ID NO: 6) is based on VH5_a; humZ270VH7 (SEQ ID NO: 7) is based on VH1_f; and humZ270VH8 (SEQ ID NO: 8) is based on VH1_46; all with a JH6 J-segment. Each of these antibodies retains high affinity binding to NKG2A, with low likelihood of a host immune response against the antibody as the 6 C-terminal amino acid residues of the Kabat CDR-H2 of each of the humanized constructs are identical to the human acceptor framework. Using the alignment program VectorNTI, the following sequence identities between humZ270VH1 and humZ270VH5, -6, -7, and -8 were obtained: 78.2% (VH1 vs. VH5), 79.0% (VH1 vs. VH6), 88.7% (VH1 vs. VH7), and 96.0% (VH1 vs. VH8).

In one aspect, the agent comprises (i) a heavy chain variable region of any of SEQ ID NOS: 4-8, or an amino acid sequence at least 50%, 60%, 70%, 80%, 90%, 95%, 98% or 99% identical thereto, and (ii) a light chain variable region of SEQ ID NO: 9, or an amino acid sequence at least 50%, 60%, 70%, 80%, 90%, 95%, 98% or 99% identical thereto. In one aspect, the agent comprises (i) a heavy chain comprising the amino acid sequence of any of SEQ ID NOS: 4-8, or an amino acid sequence at least 50%, 60%, 70%, 80%, 90%, 95%, 98% or 99% identical thereto, and (ii) a light chain comprising the amino acid sequence of SEQ ID NO: 9, or an amino acid sequence at least 50%, 60%, 70%, 80%, 90%, 95%, 98% or 99% identical thereto. The antibody having the heavy chain of any of SEQ ID NOS: 4-8 and a light chain of SEQ ID NO: 9 neutralizes the inhibitory activity of NKG2A, but does not substantially bind the activating receptors NKG2C, NKGE or NKG2H. This antibody furthermore competes with HLA-E for binding to NKG2A on the surface of a cell. In one aspect, the agent comprises HCDR1, HCDR2 and/or HCDR3 sequences derived from the heavy chain having the amino acid sequence of any of SEQ ID NO: 4-8. In one aspect of the invention, the agent comprises LCDR1, LCDR2 and/or LCDR3 sequences derived from the light chain having the amino acid sequence of SEQ ID NO: 9.

Heavy Chains
VH6:
(SEQ ID NO: 4)
<u>EVQLVQSGAEVKKPGESLKISCKGSGYSFTSYWMNWVRQMPGKGLEWM</u>
<u>GRIDPYDSETHYSPSFQGQVTISADKSISTAYLQWSSLKASDTAMYYC</u>
<u>ARGGYDFDVGTLYWFFDVWGQGTTVTVSS</u>ASTKGPSVFPLAPCSRSTS
ESTAALGCLVKDYFPEPVTVSWNSGALTSGVHTFPAVLQSSGLYSLSS
VVTVPSSSLGTKTYTCNVDHKPSNTKVDKRVESKYGPPCPPCPAPEFL
GGPSVFLFPPKPKDTLMISRTPEVTCVVVDVSQEDPEVQFNWYVDGVE
VHNAKTKPREEQFNSTYRVVSVLTVLHQDWLNGKEYKCKVSNKGLPSS
IEKTISKAKGQPREPQVYTLPPSQEEMTKNQVSLTCLVKGFYPSDIAV
EWESNGQPENNYKTTPPVLDSDGSFFLYSRLTVDKSRWQEGNVFSCSV
MHEALHNHYTQKSLSLSLGK VH1:
(SEQ ID NO: 5)
<u>QVQLVQSGAEVKKPGASVKVSCKASGYTFTSYWMNWVRQAPGQGLEWM</u>
<u>GRIDPYDSETHYAQKLQGRVTMTTDTSTSTAYMELRSLRSDDTAVYYC</u>
<u>ARGGYDFDVGTLYWFFDVWGQGTTVTVSS</u>ASTKGPSVFPLAPCSRSTS
ESTAALGCLVKDYFPEPVTVSWNSGALTSGVHTFPAVLQSSGLYSLSS
VVTVPSSSLGTKTYTCNVDHKPSNTKVDKRVESKYGPPCPPCPAPEFL
GGPSVFLFPPKPKDTLMISRTPEVTCVVVDVSQEDPEVQFNWYVDGVE
VHNAKTKPREEQFNSTYRVVSVLTVLHQDWLNGKEYKCKVSNKGLPSS
IEKTISKAKGQPREPQVYTLPPSQEEMTKNQVSLTCLVKGFYPSDIAV
EWESNGQPENNYKTTPPVLDSDGSFFLYSRLTVDKSRWQEGNVFSCSV
MHEALHNHYTQKSLSLSLGK VH5:
(SEQ ID NO: 6)
<u>EVQLVQSGAEVKKPGESLRISCKGSGYSFTSYWMNWVRQMPGKGLEWM</u>
<u>GRIDPYDSETHYSPSFQGHVTISADKSISTAYLQWSSLKASDTAMYYC</u>
<u>ARGGYDFDVGTLYWFFDVWGQGTTVTVSS</u>ASTKGPSVFPLAPCSRSTS
ESTAALGCLVKDYFPEPVTVSWNSGALTSGVHTFPAVLQSSGLYSLSS
VVTVPSSSLGTKTYTCNVDHKPSNTKVDKRVESKYGPPCPPCPAPEFL
GGPSVFLFPPKPKDTLMISRTPEVTCVVVDVSQEDPEVQFNWYVDGVE
VHNAKTKPREEQFNSTYRVVSVLTVLHQDWLNGKEYKCKVSNKGLPSS
IEKTISKAKGQPREPQVYTLPPSQEEMTKNQVSLTCLVKGFYPSDIAV
EWESNGQPENNYKTTPPVLDSDGSFFLYSRLTVDKSRWQEGNVFSCSV
MHEALHNHYTQKSLSLSLGK VH7:
(SEQ ID NO: 7)
<u>EVQLVQSGAEVKKPGATVKISCKVSGYTFTSYWMNWVQQAPGKGLEWM</u>
<u>GRIDPYDSETHYAEKFQGRVTITADTSTDTAYMELSSLRSEDTAVYYC</u>
<u>ATGGYDFDVGTLYWFFDVWGQGTTVTVSS</u>ASTKGPSVFPLAPCSRSTS
ESTAALGCLVKDYFPEPVTVSWNSGALTSGVHTFPAVLQSSGLYSLSS
VVTVPSSSLGTKTYTCNVDHKPSNTKVDKRVESKYGPPCPPCPAPEFL
GGPSVFLFPPKPKDTLMISRTPEVTCVVVDVSQEDPEVQFNWYVDGVE

```
VHNAKTKPREEQFNSTYRVVSVLTVLHQDWLNGKEYKCKVSNKGLPSS

IEKTISKAKGQPREPQVYTLPPSQEEMTKNQVSLTCLVKGFYPSDIAV

EWESNGQPENNYKTTPPVLDSDGSFFLYSRLTVDKSRWQEGNVFSCSV

MHEALHNHYTQKSLSLSLGK

VH8:
                                           (SEQ ID NO: 8)
QVQLVQSGAEVKKPGASVKVSCKASGYTFTSYWMNWVRQAPGQGLEWM

GRIDPYDSETHYAQKFQGRVTMTRDTSTSTVYMELSSLRSEDTAVYYC

ARGGYDFDVGTLYWFFDVWGQGTTVTVSSASTKGPSVFPLAPCSRSTS

ESTAALGCLVKDYFPEPVTVSWNSGALTSGVHTFPAVLQSSGLYSLSS

VVTVPSSSLGTKTYTCNVDHKPSNTKVDKRVESKYGPPCPPCPAPEFL

GGPSVFLFPPKPKDTLMISRTPEVTCVVVDVSQEDPEVQFNWYVDGVE

VHNAKTKPREEQFNSTYRVVSVLTVLHQDWLNGKEYKCKVSNKGLPSS

IEKTISKAKGQPREPQVYTLPPSQEEMTKNQVSLTCLVKGFYPSDIAV

EWESNGQPENNYKTTPPVLDSDGSFFLYSRLTVDKSRWQEGNVFSCSV

MHEALHNHYTQKSLSLSLGK

Light chain
                                           (SEQ ID NO: 9)
DIQMTQSPSSLSASVGDRVTITCRASENIYSYLAWYQQKPGKAPKLLI

YNAKTLAEGVPSRFSGSGSGTDFTLTISSLQPEDFATYYCQHHYGTPR

TFGGGTKVEIKRTVAAPSVFIFPPSDEQLKSGTASVVCLLNNFYPREA

KVQWKVDNALQSGNSQESVTEQDSKDSTYSLSSTLTLSKADYEKHKVY

ACEVTHQGLSSPVTKSFNRGEC
```

In one aspect, the anti-NKG2A antibody is an antibody comprising a CDR-H1 corresponding to residues 31-35 of SEQ ID NOS: 4-8, a CDR-H2 corresponding to residues 50-60 (optionally 50-66 when including amino acids of human origin) of SEQ ID NOS: 4-8, and a CDR-H3 corresponding to residues 99-114 (95-102 according to Kabat) of SEQ ID NOS: 4-8. In one embodiment, the CDR-H2 corresponding to residues 50-66 of SEQ ID NOS: 4-8. Optionally, a CDR may comprise one, two, three, four, or more amino acid substitutions.

In one aspect, the anti-NKG2A antibody is an antibody comprising a CDR-L1 corresponding to residues 24-34 of SEQ ID NO: 9, a CDR-L2 corresponding to residues 50-56 of SEQ ID NO: 9, and an CDR-L3 corresponding to residues 89-97 of SEQ ID NO: 9. Optionally, a CDR may comprise one, two, three, four, or more amino acid substitutions.

In one aspect, the anti-NKG2A antibody is an antibody comprising a CDR-H1 corresponding to residues 31-35 of SEQ ID NOS: 4-8, a CDR-H2 corresponding to residues 50-60 (optionally 50-66) of SEQ ID NOS: 4-8, and a CDR-H3 corresponding to residues 99-114 (95-102 according to Kabat) of SEQ ID NOS: 4-8, a CDR-L1 corresponding to residues 24-34 of SEQ ID NO: 9, a CDR-L2 corresponding to residues 50-56 of SEQ ID NO: 9, and an CDR-L3 corresponding to residues 89-97 of SEQ ID NO: 9.

In one aspect, the agent comprises HCDR1, HCDR2 and/or HCDR3 sequences derived from the VH having the amino acid sequence of SEQ ID NO: 10. In one aspect of the invention, the agent comprises LCDR1, LCDR2 and/or LCDR3 sequences derived from the VL having the amino acid sequence of SEQ ID NO: 11. In one aspect, the agent comprises HCDR1, HCDR2 and/or HCDR3 sequences derived from the VH having the amino acid sequence of SEQ ID NO: 10, and LCDR1, LCDR2 and/or LCDR3 sequences derived from the VL having the amino acid sequence of SEQ ID NO: 11. The antibody having the heavy chain of SEQ ID NO: 10 and a light chain of SEQ ID NO: 11 neutralizes the inhibitory activity of NKG2A, and also binds the activating receptors NKG2C, NKG2E or NKG2H. The antibody does not competes with HLA-E for binding to NKG2A on the surface of a cell (i.e. it is a non-competitive antagonist of NKG2A).

```
                                          (SEQ ID NO: 10)
EVQLVESGGGLVKPGGSLKLSCAASGFTFSSYAMSWVRQSPEKRLEWV

AEISSGGSYTYYPDTVTGRFTISRDNAKNTLYLEISSLRSEDTAMYYC

TRHGDYPRFFDVWGAGTTVTVSS (SEQ ID NO: 11)
QIVLTQSPALMSASPGEKVTMTCSASSSVSYIYWYQQKPRSSPKPWIY

LTSNLASGVPARFSGSGSGTSYSLTISSMEAEDAATYYCQQWSGNPYT

FGGGTKLEIKR
```

In one aspect, the agent comprises amino acid residues 31-35, 50-60, 62, 64, 66, and 99-108 of the variable-heavy ($V_H$) domain (SEQ ID NO: 10) and amino acid residues 24-33, 49-55, and 88-96 of the variable-light ($V_L$) domain (SEQ ID NO: 11), optionally with one, two, three, four, or more amino acid substitutions.

In one aspect, the agent is a fully human antibody which has been raised against the CD94/NKG2A epitope to which any of the aforementioned antibodies bind.

It will be appreciated that, while the aforementioned antibodies can be used, other antibodies can recognize and be raised against any part of the NKG2A polypeptide so long as the antibody causes the neutralization of the inhibitory activity of NKG2A. For example, any fragment of NKG2A, preferably but not exclusively human NKG2A, or any combination of NKG2A fragments, can be used as immunogens to raise antibodies, and the antibodies can recognize epitopes at any location within the NKG2A polypeptide, so long as they can do so on NKG2A expressing NK cells as described herein. Optionally, the epitope is the epitope specifically recognized by antibody having the heavy chain of SEQ ID NOS: 4-8 and the light chain of SEQ ID NO: 9.

In one aspect, the agent competes with humZ270 antibody disclosed in U.S. Pat. No. 8,206,709 (the disclosure of which is incorporated herein by reference) in binding to the extracellular portion of human CD94/NKG2A receptor. Competitive binding can be measured, for instance, in BiaCore experiments, in which the capacity of agents is measured, for binding the extracellular portion of immobilized CD94/NKG2A receptor (e.g. purified from CD94/NKG2 expressing cells, or produced in a bio-system) saturated with humZ270. Alternatively, the binding of agents to cells is measured that either naturally express, or over-express (e.g. after transient or stable transfection), CD94/NKG2A receptor, and which have been pre-incubated with saturating doses of Z270. In one embodiment, competitive binding can be measured using the methods disclosed in U.S. Pat. No. 8,206,709, for example by assessing binding to Ba/F3-CD94-NKG2A cells by flow cytometry as shown in Example 15 of U.S. Pat. No. 8,206,709, the disclosure of which is incorporate herein by reference.

PD-1 Neutralizing Therapeutic Agents

There are currently at least six agents blocking the PD-1/PD-L1 pathway that are marketed or in clinical evaluation.

One agent is BMS-936558 (Nivolumab/ONO-4538, Bristol-Myers Squibb; formerly MDX-1106). Nivolumab, (Trade name Opdivo®) is an FDA-approved fully human IgG4 anti-PD-L1 mAb that inhibits the binding of the PD-L1 ligand to both PD-1 and CD80 and is described as antibody 5C4 in WO 2006/121168, the disclosure of which is incorporated herein by reference. For melanoma patients, the most significant OR was observed at a dose of 3 mg/kg, while for other cancer types it was at 10 mg/kg. Nivolumab is generally dosed at 10 mg/kg every 3 weeks until cancer progression.

MK-3475 (human IgG4 anti-PD1 mAb from Merck), also referred to as lambrolizumab or pembrolizumab (Trade name Keytruda®) has been approved by the FDA for the treatment of melanoma and is being tested in other cancers. Pembrolizumab was tested at 2 mg/kg or 10 mg/kg every 2 or 3 weeks until disease progression. DNA constructs encoding the variable regions of the heavy and light chains of the humanized antibodies h409All have been deposited with the American Type Culture Collection Patent Depository (10801 University Blvd., Manassas, Va.). The plasmid containing the DNA encoding the heavy chain of h409A-I 1 was deposited on Jun. 9, 2008 and identified as 081469_SPD-H and the plasmid containing the DNA encoding the light chain of h409AI 1 was deposited on Jun. 9, 2008 and identified as 0801470SPD-L-I 1. MK-3475, also known as Merck 3745 or SCH-900475, is also described in WO2009/114335.

MPDL3280A/RG7446 (anti-PD-L1 from Roche/Genentech) is a human anti-PD-L1 mAb that contains an engineered Fc domain designed to optimize efficacy and safety by minimizing FcγR binding and consequential antibody-dependent cellular cytotoxicity (ADCC). Doses of ≤1, 10, 15, and 25 mg/kg MPDL3280A were administered every 3 weeks for up to 1 year. In phase 3 trial, MPDL3280A is administered at 1200 mg by intravenous infusion every three weeks in NSCLC.

AMP-224 (Amplimmune and GSK) is an immunoadhesin comprising a PD-L2 extracellular domain fused to an Fc domain. Other examples of agents that neutralize PD-1 may include an antibody that binds PD-L2 (an anti-PD-L2 antibody) and blocks the interaction between PD-1 and PD-L2.

Pidlizumab (CT-011; CureTech) (humanized IgG1 anti-PD1 mAb from CureTech/Teva), Pidlizumab (CT-011; CureTech) (see e.g., WO2009/101611) Thirty patients with rituximab-sensitive relapsed FL were treated with 3 mg/kg intravenous CT-011 every 4 weeks for 4 infusions in combination with rituximab dosed at 375 mg/m2 weekly for 4 weeks, starting 2 weeks after the first infusion of CT-011.

Further known PD-1 antibodies and other PD-1 inhibitors include AMP-224 (a B7-DC/IgG1 fusion protein licensed to GSK), AMP-514 described in WO 2012/145493, antibody MEDI-4736 (an anti-PD-L1 developed by AstraZeneca/Medimmune) described in WO2011/066389 and US2013/034559, antibody YW243.55.S70 (an anti-PD-L1) described in WO2010/077634, MDX-1105, also known as BMS-936559, is an anti-PD-L1 antibody developed by Bristol-Myers Squibb described in WO2007/005874, and antibodies and inhibitors described in WO2006/121168, WO2009/014708, WO2009/114335 and WO2013/019906, the disclosures of which are hereby incorporated by reference. Further examples of anti-PD1 antibodies are disclosed in WO2015/085847 (Shanghai Hengrui Pharmaceutical Co. Ltd.), for example antibodies having light chain variable domain CDR1, 2 and 3 of SEQ ID NO: 6, SEQ ID NO: 7 and/or SEQ ID NO: 8, respectively, and antibody heavy chain variable domain CDR1, 2 and 3 of SEQ ID NO: 3, SEQ ID NO: 4 or SEQ ID NO: 5, respectively, wherein the SEQ ID NO references are the numbering according to WO2015/085847, the disclosure of which is incorporated herein by reference. Antibodies that compete with any of these antibodies for binding to PD-1 or PD-L1 also can be used.

An exemplary anti-PD-1 antibody is pembrolizumab (see, e.g., WO 2009/114335 the disclosure of which is incorporated herein by reference.). The anti-PD-1 antibody may be the antibody h409AI 1 in WO 2008/156712, comprising heavy chain variable regions encoded by the DNA deposited at the ATCC as 081469_SPD-H and light chain variable regions encoded by the DNA deposited at the ATCC as 0801470_SPD-L-I 1. In other embodiments, the antibody comprises the heavy and light chain CDRs or variable regions of pembrolizumab. Accordingly, in one embodiment, the antibody comprises the CDR1, CDR2, and CDR3 domains of the VH of pembrolizumab encoded by the DNA deposited at the ATCC as 081469_SPD-H, and the CDR1, CDR2 and CDR3 domains of the VL of pembrolizumab encoded by the DNA deposited at the ATCC as 0801470_SPD-L-I 1.

In some embodiments, the PD-1 neutralizing agent is an anti-PD-L1 mAb that inhibits the binding of PD-L1 to PD-1. In some embodiments, the PD-1 neutralizing agent is an anti-PD1 mAb that inhibits the binding of PD-1 to PD-L1. In some embodiments, the PD-1 neutralizing agent is an immunoadhesin (e.g., an immunoadhesin comprising an extracellular or PD-1 binding portion of PD-L1 or PD-L2 fused to a constant region (e.g., an Fc region of an immunoglobulin sequence).

Another exemplary anti-PD-1 antibody is nivolumab comprising heavy and light chains having the respective sequences shown in SEQ ID NOs: 12 and 13 or a respective amino acid sequence at least 50%, 60%, 70%, 80%, 90%, 95%, 98% or 99% identical thereto, or antigen binding fragments and variants thereof. In other embodiments, the antibody comprises the heavy and light chain CDRs or variable regions of nivolumab. Accordingly, in one embodiment, the antibody comprises the CDR1, CDR2, and CDR3 domains of the heavy chain of nivolumab having the sequence set forth in SEQ ID NO: 12, and the CDR1, CDR2 and CDR3 domains of the light chain of nivolumab having the sequences set forth in SEQ ID NO: 13.

```
                                             (SEQ ID NO: 12)
QVQLVESGGGWQPGRSLRLDCKASGITFSNSGMHWVRQAPGKGLEWVA

VrWYDGSKRYYADSVKGRFTISRDNSKNTLFLQMNSLRAEDTAVYYCA

TNDDYWGQGTLVTVSSASTKGPSVFPLAPCSRSTSESTAALGCLVDYF

PEPVTVSWNSGALTSGVHTFPAVLQSSGLYSLSSVVTVPSSSLGTTYT

CNVDHKPSNTKVDRVESYGPPCPPCPAPEFLGGPSVFLFPPKPKDTLM

ISRTPEVTCWVDVSQEDPEVQFNWYYDGVEVHNATKPREEQFNSTYRV

VSVLTVLHQDWLNGKEYKCKVSNKGLPSSIEKTISKAGQPREPQVYTL

PPSQEEMTKNQVSLTCLVKGFYPSDIAVEWESNGQPEKNYKTTPPVLD

SDGSFFLYSRLTVDKSRWQEGNVFSCSVMHEALHNHYTQKSLSLSLGK.

(SEQ ID NO: 13)
EIVLTQSPATLSLSPGERATLSCRASQSVSSYLAWYQQPGQAPRLLIY

DASNRATGIPARFSGSGSGTDFTLTISSLEPEDFAVYYCQQSSNWPRT

FGQGTKVEIRTVAAPSVFIFPPSDEQLSGTASVVCLLNNFYPREAVQW
```

-continued

KVDNALQSGNSQESVTEQDSDSTYSLSSTLLSKADYEKHKVYACEVTH

QGLSSPVTSFNRGEC.

An exemplary anti-PD-L1 antibody comprises heavy and light chain variable regions having the respective sequences shown in SEQ ID NOs: 14 and 15, or an amino acid sequence at least 50%, 60%, 70%, 80%, 90%, 95%, 98% or 99% identical thereto respectively, or antigen binding fragments and variants thereof. In other embodiments, the antibody comprises the heavy and light chain CDRs or variable regions of MPDL3280A. Accordingly, in one embodiment, the antibody comprises the CDR1, CDR2, and CDR3 domains of the heavy chain having the sequence set forth in SEQ ID NO: 14, and the CDR1, CDR2 and CDR3 domains of the light chain having the sequences set forth in SEQ ID NO: 15.

(SEQ ID NO: 14)
EVQLVESGGGLVQPGGSLRLSCAASGFTFSDSWIHWVRQAPGKGLEWV

AWISPYGGSTYYADSVKGRFTISADTSKNTAYLQNSLRAEDTAVYYCA

RRHWPGGFDYWGQGTLVTVSS (SEQ ID NO: 15)
DIQMTQSPSSLSASVGDRVTITCRASQDVSTAVAWYQQPGKAPKLLIY

SASFLYSGVPSRFSGSGSGTDFTLTISSLQPEDFATYYCQQYLYHPAT

FGQGTKVEIKR

The anti-PD-1 or anti-PD-L1 antibody can be selected from a fully human antibody, a humanized antibody, and a chimeric antibody. In one aspect of the invention, the agent comprises a constant domain derived from a human IgG1, IgG2, IgG3 or IgG4 antibody. In one aspect of the invention, the agent is a fragment of an antibody selected from IgA, an IgD, an IgG, an IgE and an IgM antibody. In one aspect of the invention, the agent is an antibody fragment selected from a Fab fragment, a Fab' fragment, a Fab'-SH fragment, a F(ab)2 fragment, a F(ab')2 fragment, an Fv fragment, a Heavy chain Ig (a llama or camel Ig), a $V_{HH}$ fragment, a single domain FV, and a single-chain antibody fragment. In one aspect of the invention, the agent is a synthetic or semisynthetic antibody-derived molecule selected from a scFV, a dsFV, a minibody, a diabody, a triabody, a kappa body, an IgNAR; and a multispecific antibody.

The anti-PD-1 or anti-PD-L1 antibody can lack substantial specific binding to Fcγ receptors, e.g. CD16. Such antibodies may comprise constant regions of various heavy chains that are known not to bind Fc receptors. One such example is an IgG4 constant region. IgG4 Alternatively, antibody fragments that do not comprise constant regions, such as Fab or F(ab')2 fragments, can be used to avoid Fc receptor binding. Fc receptor binding can be assessed according to methods known in the art, including for example testing binding of an antibody to Fc receptor protein in a BIACORE assay. Also, any human antibody type (e.g. IgG1, IgG2, IgG3 or IgG4) can be used in which the Fc portion is modified to minimize or eliminate binding to Fcγ receptors. The anti-PD-1 or anti-PDL1 antibody, the antibody will therefore typically have reduced or minimal effector function. In one aspect, the minimal effector function results from production in prokaryotic cells. In one aspect the minimal effector function results from an "effector-less Fc mutation" or aglycosylation. In still a further embodiment, the effector-less Fc mutation is an N297A or D265A/N297A substitution in the constant region.

Formulations

An anti-NKG2A or anti-PD-1 or anti-PD-L1 agent such as an antibody can be incorporated in a pharmaceutical formulation comprising in a concentration from 1 mg/ml to 500 mg/ml, wherein said formulation has a pH from 2.0 to 10.0. The formulation may further comprise a buffer system, preservative(s), tonicity agent(s), chelating agent(s), stabilizers and surfactants. In one embodiment, the pharmaceutical formulation is an aqueous formulation, i.e., formulation comprising water. Such formulation is typically a solution or a suspension. In a further embodiment, the pharmaceutical formulation is an aqueous solution. The term "aqueous formulation" is defined as a formulation comprising at least 50% w/w water. Likewise, the term "aqueous solution" is defined as a solution comprising at least 50% w/w water, and the term "aqueous suspension" is defined as a suspension comprising at least 50% w/w water.

In another embodiment, the pharmaceutical formulation is a freeze-dried formulation, whereto the physician or the patient adds solvents and/or diluents prior to use.

In another embodiment, the pharmaceutical formulation is a dried formulation (e.g. freeze-dried or spray-dried) ready for use without any prior dissolution.

In a further aspect, the pharmaceutical formulation comprises an aqueous solution of such an antibody, and a buffer, wherein the antibody is present in a concentration from 1 mg/ml or above, and wherein said formulation has a pH from about 2.0 to about 10.0.

In a another embodiment, the pH of the formulation is in the range selected from the list consisting of from about 2.0 to about 10.0, about 3.0 to about 9.0, about 4.0 to about 8.5, about 5.0 to about 8.0, and about 5.5 to about 7.5.

In a further embodiment, the buffer is selected from the group consisting of sodium acetate, sodium carbonate, citrate, glycylglycine, histidine, glycine, lysine, arginine, sodium dihydrogen phosphate, disodium hydrogen phosphate, sodium phosphate, and tris(hydroxymethyl)-aminomethan, bicine, tricine, malic acid, succinate, maleic acid, fumaric acid, tartaric acid, aspartic acid or mixtures thereof. Each one of these specific buffers constitutes an alternative embodiment of the invention.

In a further embodiment, the formulation further comprises a pharmaceutically acceptable preservative. In a further embodiment, the formulation further comprises an isotonic agent. In a further embodiment, the formulation also comprises a chelating agent. In a further embodiment of the invention the formulation further comprises a stabilizer. In a further embodiment, the formulation further comprises a surfactant. For convenience reference is made to Remington: *The Science and Practice of Pharmacy*, 19th edition, 1995.

It is possible that other ingredients may be present in the peptide pharmaceutical formulation of the present invention. Such additional ingredients may include wetting agents, emulsifiers, antioxidants, bulking agents, tonicity modifiers, chelating agents, metal ions, oleaginous vehicles, proteins (e.g., human serum albumin, gelatine or proteins) and a zwitterion (e.g., an amino acid such as betaine, taurine, arginine, glycine, lysine and histidine). Such additional ingredients, of course, should not adversely affect the overall stability of the pharmaceutical formulation of the present invention.

Administration of pharmaceutical compositions according to the invention may be through several routes of administration, for example, intravenous. Suitable antibody formulations can also be determined by examining experiences with other already developed therapeutic monoclonal antibodies. Several monoclonal antibodies have been shown to be efficient in clinical situations, such as Rituxan (Rituximab), Herceptin (Trastuzumab) Xolair (Omalizumab), Bexxar (Tositumomab), Campath (Alemtuzumab), Zevalin, Oncolym and similar formulations may be used with the antibodies of this invention. For example, a monoclonal antibody can be supplied at a concentration of 10 mg/mL in either 100 mg (10 mL) or 500 mg (50 mL) single-use vials, formulated for IV administration in 9.0 mg/mL sodium chloride, 7.35 mg/mL sodium citrate dihydrate, 0.7 mg/mL polysorbate 80, and Sterile Water for Injection. The pH is adjusted to 6.5. In another embodiment, the antibody is supplied in a formulation comprising about 20 mM Na-Citrate, about 150 mM NaCl, at pH of about 6.0.

Also provided are kits which include a pharmaceutical composition containing an anti-NKG2A antibody, and an anti-PD-1 or anti-PD-L1 antibody, and a pharmaceutically-acceptable carrier, in a therapeutically effective amount adapted for use in the preceding methods. The kits optionally also can include instructions, e.g., comprising administration schedules, to allow a practitioner (e.g., a physician, nurse, or patient) to administer the composition contained therein to administer the composition to a patient having cancer (e.g., a solid tumor). The kit also can include a syringe.

Optionally, the kits include multiple packages of the single-dose pharmaceutical compositions each containing an effective amount of the anti-NKG2A, anti-PD-1 or PD-L1 antibody for a single administration in accordance with the methods provided above. Instruments or devices necessary for administering the pharmaceutical composition(s) also may be included in the kits. For instance, a kit may provide one or more pre-filled syringes containing an amount of the anti-NKG2A, anti-PD-1 or anti-PD-L1 antibody.

In one embodiment, the present invention provides a kit for treating a cancer in a human patient, the kit comprising:
(a) a dose of an anti-NKG2A antibody comprising the CDR1, CDR2 and CDR3 domains of a heavy chain having the sequence set forth in any of SEQ ID NOS: 4-8, and the CDR1, CDR2 and CDR3 domains of a light chain having the sequence set forth in SEQ ID NO: 9;
(b) a dose of an anti-PD-1 antibody or an anti-PD-L1 antibody; and
(c) optionally, instructions for using the anti-NKG2A antibody and anti-PD-1 antibody in any of the methods described herein.

Diagnostics, Prognostics, and Treatment of Malignancies

Described are methods useful in the diagnosis, prognosis, monitoring, treatment and prevention of a cancer in an individual. While the treatment regimens and methods described herein are particularly useful for the treatment of solid tumors, the treatment regimens and methods described herein can also be used for a variety of hematological cancers, as well as infectious disease, and inflammation and autoimmune disorders. The methods and compositions of the present invention are utilized for example the treatment of a variety of cancers and other proliferative diseases including, but not limited to: carcinoma, including that of the bladder, breast, colon, kidney, liver, lung, ovary, prostate, pancreas, stomach, cervix, thyroid and skin; hematopoietic tumors of lymphoid lineage, including leukemia, acute lymphocytic leukemia, chronic lymphocytic leukemia, acute lymphoblastic leukemia, B-cell lymphoma, T-cell lymphoma, Hodgkins lymphoma, non-Hodgkins lymphoma, hairy cell lymphoma and Burketts lymphoma, and multiple myeloma; hematopoietic tumors of myeloid lineage, including acute and chronic myelogenous leukemias, promyelocytic leukemia, and myelodysplastic syndrome; tumors of mesenchymal origin, including fibrosarcoma and rhabdomyoscarcoma; other tumors, including melanoma, seminoma, terato-carcinoma, neuroblastoma and glioma; tumors of the central and peripheral nervous system, including astrocytoma, neuroblastoma, glioma, and schwannomas; tumors of mesenchymal origin, including fibrosarcoma, rhabdomyoscaroma, and osteosarcoma; and other tumors, including melanoma, xeroderma pigmentosum, keratoacanthoma, seminoma, and thyroid follicular cancer.

Combination therapies for the treatment of cancer provided herein involve administration of a neutralizing anti-NKG2A antibody and a PD-1-neutralizing agent, e.g. neutralizing anti-PD-1 or anti-PD-L1 antibody, to treat subjects afflicted with cancer (e.g., advanced refractory solid tumors). In one embodiment, the invention provides an anti-NKG2A antibody and an anti-PD-1 antibody in combination to treat subjects having a solid tumor (e.g., a solid tumor, an advanced refractory solid tumor) or subjects having a hematological tumor. In a particular embodiment, the anti-NKG2A antibody comprises a heavy chain of any of SEQ ID NOS: 4-8 and a light chain of SEQ ID NO: 9. In one embodiment, the antibody that neutralizes the inhibitory activity of PD-1 is selected from the group consisting of pembrolizumab, nivolumab, AMP-514, MEDI-4736, CT-011 and MPDL3280A.

As used herein, adjunctive or combined administration (co-administration) includes simultaneous administration of the compounds in the same or different dosage form, or separate administration of the compounds (e.g., sequential administration). Thus, the anti-NKG2A and anti-PD-1 or anti-PD-L1 antibodies can be simultaneously administered in a single formulation. Alternatively, the anti-NKG2A and anti-PD-1 or anti-PD-L1 antibodies can be formulated for separate administration and are administered concurrently or sequentially.

In one embodiment, the cancer treated with the methods disclosed herein is an HLA-E-expressing cancer. In one embodiment, the cancer is selected from the group consisting of lung cancer (e.g. non-small cell lung cancer (NSCLC)), renal cell carcinoma (RCC), melanoma, colorectal cancer, and ovarian cancer.

A patient having a cancer can be treated with the anti-NKG2A agents with or without a prior detection step to assess expression of HLA-E on the surface of tumor cells. Advantageously, the treatment methods can comprises a step of detecting a HLA-E nucleic acid or polypeptide in a biological sample of a tumor (e.g. on a tumor cell) from an individual. Example of biological samples include any suitable biological fluid (for example serum, lymph, blood), cell sample, or tissue sample. For example, a tissue sample may be a sample of tumor tissue or tumor-adjacent tissue. Optionally, HLA-E polypeptide is detected on the surface of a malignant cell. A determination that a biological sample expresses HLA-E (e.g. prominently expresses; expresses HLA-E at a high level, high intensity of staining with an anti-HLA-E antibody, compared to a reference) indicates that the individual has a cancer that may have a strong benefit from treatment with an agent that inhibits NKG2A. In one embodiment, the method comprises determining the level of expression of a HLA-E nucleic acid or polypeptide in a biological sample and comparing the level to a reference level (e.g. a value, weak cell surface staining, etc.) corresponding to a healthy individual. A determination that a biological sample expresses an HLA-E nucleic acid or polypeptide at a level that is increased compared to the reference level indicates that the individual has a cancer that can be treated with an agent that inhibits NKG2A.

In one embodiment, a determination that a biological sample (e.g. a sample comprising tumor cells, tumor tissue and/or tumor adjacent tissue) prominently expresses HLA-E nucleic acid or polypeptide indicates that the individual has a cancer that can be treated with an agent that inhibits NKG2A. "Prominently expressed", when referring to a HLA-E polypeptide, means that the HLA-E polypeptide is expressed in a substantial number of tumor cells taken from a given individual. While the definition of the term "prominently expressed" is not bound by a precise percentage value, in some examples a receptor said to be "prominently expressed" will be present on at least 30%, 40%, 50°%, 60%, 70%, 80%, or more of the tumor cells taken from a patient (in a sample).

Determining whether an individual has cancer cells that express an HLA-E polypeptide can for example comprise obtaining a biological sample (e.g. by performing a biopsy) from the individual that comprises cancer cells, bringing said cells into contact with an antibody that binds an HLA-E polypeptide, and detecting whether the cells express HLA-E on their surface. Optionally, determining whether an individual has cancer cells that express HLA-E comprises conducting an immunohistochemistry assay. Optionally determining whether an individual has cancer cells that express HLA-E comprises conducting a flow cytometry assay.

In the treatment methods, the anti-NKG2A antibody and the anti-PD-1 or anti-PD-L1 antibodies can be administered separately, together or sequentially, or in a cocktail. In some embodiments, the antigen-binding compound is administered prior to the administration of the anti-PD-1 or anti-PD-L1 antibodies. For example, the anti-NKG2A antibody can be administered approximately 0 to 30 days prior to the administration of the anti-PD-1 or anti-PD-L1 antibodies. In some embodiments, an anti-NKG2A antibody is administered from about 30 minutes to about 2 weeks, from about 30 minutes to about 1 week, from about 1 hour to about 2 hours, from about 2 hours to about 4 hours, from about 4 hours to about 6 hours, from about 6 hours to about 8 hours, from about 8 hours to 1 day, or from about 1 to 5 days prior to the administration of the anti-PD-1 or anti-PD-L1 antibodies. In some embodiments, an anti-NKG2A antibody is administered concurrently with the administration of the anti-PD-1 or anti-PD-L1 antibodies. In some embodiments, an anti-NKG2A antibody is administered after the administration of the anti-PD-1 or anti-PD-L1 antibodies. For example, an anti-NKG2A antibody can be administered approximately 0 to 30 days after the administration of the anti-PD-1 or anti-PD-L1 antibodies. In some embodiments, an anti-NKG2A antibody is administered from about 30 minutes to about 2 weeks, from about 30 minutes to about 1 week, from about 1 hour to about 2 hours, from about 2 hours to about 4 hours, from about 4 hours to about 6 hours, from about 6 hours to about 8 hours, from about 8 hours to 1 day, or from about 1 to 5 days after the administration of the anti-PD-1 or anti-PD-L1 antibodies.

Suitable treatment protocols for treating a human having cancer include, for example, administering to the patient an effective amount of each of an antibody that inhibits NKG2A and an antibody that neutralizes the inhibitory activity of human PD-1, wherein the method comprises at least one administration cycle in which at least one dose of the anti-NKG2A antibody is administered at a dose of 1-10 mg/kg body weight and at least one dose of the anti-PD-1 or anti-PD-L1 antibody is administered at a dose of 1-20 mg/kg body weight. In one embodiment, the administration cycle is between 2 weeks and 8 weeks.

In one embodiment, the method comprises at least one administration cycle, wherein the cycle is a period of eight weeks or less, wherein for each of the at least one cycles, two, three or four doses of the anti-NKG2A antibody are administered at a dose of 1-10 mg/kg body weight and two, three or four doses of the anti-PD-1 or anti-PD-L1 antibody are administered at a dose of 1-20 mg/kg body weight.

The anti-NKG2A antibody can advantageously be administered in an amount that achieves a concentration in circulation that is at least 10, 20, or 30 times higher than the concentration required for substantially full (e.g., 90%, 95%) receptor saturation (e.g., as assessed by titrating anti-NKG2A antibody on NKG2A-expressing cells, for example in PBMC), or optionally in an amount that achieves a concentration in a extravascular tissue (e.g. the tumor tissue or environment) that is at least 10, 20, or 30 times higher than the concentration required for substantially full receptor saturation (e.g., as assessed by titrating anti-NKG2A antibody on NKG2A-expressing cells, for example in PBMC).

NKG2A+NK cell response can be assessed using a suitable assay of cytotoxic activity of NKG2A-expressing NK cells toward HLA-E expressing target cells. Examples include assays based on markers of NK cell activation, for example CD107 or CD137 expression. The $EC_{50}$ for NKG2A+NK cell response (e.g., as assessed in a CD107 mobilization assay) of blocking anti-NKG2A antibody humZ270 used in the Examples herein (e.g. having the heavy chain of any of SEQ ID NOS: 4-8 and a light chain of SEQ ID NO: 9) is about 4 µg/ml, and the $EC_{100}$ is about 10 µg/ml. Thus an amount of anti-NKG2A antibody is administered so at to maintain a continuous (minimum) blood concentration of at least 4 µg/ml. Advantageously an amount of anti-NKG2A antibody can be administered so at to achieve and/or maintain a continuous (minimum) blood concentration of at least 10 µg/ml. For example, the blood concentration to be achieved and/or maintained can be between 10-12 µg/ml, 10-15 µg/ml, 10-20 µg/ml, 10-30 µg/ml, 10-40 µg/ml, 10-50 µg/ml, 10-70 µg/ml, 10-100 µg/ml, 10-150 µg/ml or 10-200 µg/ml. When tissues outside of the vasculature are targeted (e.g. in the treatment of solid tumors), an amount of anti-NKG2A antibody is administered so at to achieve and/or maintain a tissue concentration of at least 10 µg/ml; for example, administering an amount of anti-NKG2A antibody to achieve a blood concentration of at least 100 µg/ml is expected to achieve a tissue concentration of at least 10 µg/ml. For example, the blood concentration to be achieved and/or maintained in order to achieve/maintain 10 µg/ml in a tissue can be between 100-110 µg/ml, 100-120 µg/ml, 100-130 µg/ml, 100-140 µg/ml, 100-150 µg/ml, 100-200 µg/ml, 100-250 µg/ml or 100-300 µg/ml.

In some embodiments, an amount of anti-NKG2A antibody is administered so as to obtain a concentration in blood (e.g., blood serum) that corresponds to at least the $EC_{50}$ for NKG2A+ lymphocyte cell response (e.g., the NKG2A+NK cell response), optionally at about or at least about, the $EC_{100}$. "$EC_{50}$" (or "$EC_{100}$") with respect to NKG2A+ cell response (e.g. NK cell response), refers to the efficient concentration of anti-NKG2A antibody which produces 50% (or 100% when referring to the $EC_{100}$) of its maximum response or effect with respect to such NKG2A+ cells response (e.g. NK cell response). In some embodiments, particularly for the treatment of solid tumors, the concentration achieved is designed to lead to a concentration in tissues (outside of the vasculature, e.g. in the tumor environment) that corresponds to at least the $EC_{50}$ for NKG2A+ NK cell response, optionally at about, or at least about, the $EC_{100}$ for NKG2A+NK cell response.

Suitable treatment protocols for an anti-NKG2A antibody such as humZ270 used in the Examples herein having an $EC_{100}$ for NKG2A+NK cell response of about 10 µg/ml comprise at least one administration cycle in which at least one dose of the anti-NKG2A antibody is administered at a dose of 2-10 mg/kg, optionally 4-10 mg/kg, optionally 6-10 mg/kg, optionally 2-6 mg/kg, optionally 2-8 mg/kg, or optionally 2-4 mg/kg body weight. Optionally, at least 2, 3, 4, 5, 6, 7 or 8 doses of the anti-NKG2A antibody are administered. In one embodiment, the administration cycle is between 2 weeks and 8 weeks. In one embodiment, the administration cycle is 8 weeks. In one embodiment, the administration cycle is 8 weeks and comprises administering one dose of the anti-NKG2A antibody every two weeks (i.e. a total of four doses).

In one aspect of any of the embodiments herein, the anti-NKG2A antibody is administered once about every two weeks.

Suitable treatment protocols for use with an anti-NKG2A antibody, particularly for the treatment of a hematopoietic tumor, include for example, administering to the patient an anti-NKG2A antibody two times per month in an amount effective to maintain a continuous blood concentration of anti-NKG2A antibody of at least 10 µg/ml between at least two successive administrations of the anti-NKG2A antibody is between 2-10 mg/kg, optionally 2-6 mg/kg, optionally 2-8 mg/kg, optionally 2-4 mg/kg, optionally 2-6 mg/kg, optionally 2-4 mg/kg, optionally about 4 mg/kg body weight. These doses can optionally be administered so as to provide for continued blood concentration of anti-NKG2A antibody of at least 10 µg/ml throughout the treatment cycle. Achieving blood concentration of anti-NKG2A antibody of 10 µg/ml corresponds to the $EC_{100}$ for an antibody such as humanized Z270.

Suitable treatment protocols for use with an anti-NKG2A antibody, particularly for the treatment of a solid tumor where anti-NKG2A antibody $EC_{50}$ concentration is sought in extravascular tissue (e.g., in the tumor or tumor environment), include for example, administering to the patient an anti-NKG2A antibody two times per month in an amount effective to maintain a continuous blood concentration of anti-NKG2A antibody of at least 40 µg/ml between at least two successive administrations of the anti-NKG2A antibody is between 2-10 mg/kg, optionally 2-6 mg/kg, optionally 2-4 mg/kg, optionally about 4 mg/kg body weight. These doses can optionally be administered so as to provide for continued blood concentration of anti-NKG2A antibody of at least 40 µg/ml throughout the treatment cycle. Achieving blood concentration of anti-NKG2A antibody of 40 µg/ml is expected to provide a tissue (e.g., extravascular tissue, tumor environment) concentration of about 4 µg/ml, in turn corresponding to the $EC_{50}$ for an antibody such as humanized Z270.

Suitable treatment protocols for use with an anti-NKG2A antibody, particularly for the treatment of a solid tumor where anti-NKG2A antibody $EC_{50}$ concentration is sought in extravascular tissue (e.g., in the tumor or tumor environment), include for example, administering to the patient an effective amount of an anti-NKG2A antibody, wherein the antibody is administered 2 times per month and the amount effective to maintain a continuous blood concentration of anti-NKG2A antibody of at least 100 µg/ml between at least two successive administrations of the anti-NKG2A antibody is between 4-10 mg/kg, optionally 4-6 mg/kg, optionally 4-8 mg/kg, optionally about 4 mg/kg, optionally about 6 mg/kg, optionally about 8 mg/kg, or optionally about 10 mg/kg. These doses can optionally be administered so as to provide for continued blood concentration of anti-NKG2A antibody of at least 100 µg/ml throughout the treatment cycle. Achieving blood concentration of anti-NKG2A antibody of 100 µg/ml is expected to provide a tissue (e.g., extravascular, tumor environment) concentration of about 10 µg/ml, in turn corresponding to the $EC_{100}$ for an antibody such as humanized Z270.

Further suitable treatment protocols for use with an anti-NKG2A antibody include regimens that employ a loading period with a higher dose, followed by a maintenance period. For example, a loading period may comprise administering to the patient an effective amount of an anti-NKG2A antibody, wherein the antibody is administered one or more times in an amount effective to maintain a continuous blood concentration of anti-NKG2A antibody of at least 100 µg/ml until the first administration of anti-NKG2A antibody in the maintenance regimen. For example, when administered once, a loading dose of 10 mg/kg of anti-NKG2A antibody can be administered, wherein the first administration of anti-NKG2A antibody within the maintenance regimen occurs about two weeks (or less) after the loading dose. The maintenance regimen can then employ a lower dose and/or lower frequency of administration in order to maintain a continuous blood concentration of anti-NKG2A antibody of at least 100 µg/ml between successive administrations within the maintenance regimen. For example, a maintenance regimen can comprise administering anti-NKG2A antibody every two weeks at a dose of between 2-10 mg/kg, optionally 4-10 mg/kg, optionally 2-4 mg/kg, optionally 4-6 mg/kg, optionally 4-8 mg/kg, optionally about 4 mg/kg, optionally about 6 mg/kg, optionally about 8 mg/kg.

In certain embodiments, a dose (e.g. each dose) of the anti-NKG2A antibody is administered at 4, 6, 8 or 10 mg/kg. In certain embodiments, a dose (e.g. each dose) of the anti-PD-1 antibody is administered at 1-20 mg/kg, optionally at 10 mg/kg. In certain embodiments, a dose (e.g. each dose) of the anti-PD-L1 antibody is administered at 10, 15, 20 or 25 mg/kg, optionally at 1200 mg total dose. In certain embodiments, the combined therapy permits the anti-PD-1 or PD-L1 antibody to be administered at a lower dose; in one embodiment, each dose of the anti-PD-1 antibody is administered at 2 or 3 mg/kg.

In one embodiment, the anti-NKG2A antibody and anti-PD-1 or anti-PD-L1 antibody are administered at the following doses:
 (a) 1-10 mg/kg anti-NKG2A antibody and (i) 1-10 mg/kg of anti-PD-1 antibody or (ii) 1-20 mg/kg of anti-PD-L1 antibody;
 (b) 4, 6, 8 or 10 mg/kg anti-NKG2A antibody and 10 mg/kg of anti-PD-1 or anti-PD-L1 antibody;
 (c) 4, 6, 8 or 10 mg/kg anti-NKG2A antibody and 3 mg/kg of anti-PD-1 antibody; or
 (d) 4, 6, 8 or 10 mg/kg anti-NKG2A antibody and 2 mg/kg of anti-PD-1 antibody.

In one aspect of any of the embodiments herein, the anti-NKG2A antibody is administered once about every two weeks. In one aspect of any of the embodiments herein, the anti-PD-1 or anti-PD-L1 antibody is administered once about every three weeks. In one aspect of any of the embodiments herein, the anti-PD-1 or anti-PD-L1 antibody is administered once about every two weeks. In one aspect of any of the embodiments herein, the anti-PD-1 or anti-PD-L1 antibody is administered once about every four weeks.

In one embodiment the anti-PD-1 or anti-PD-L1 antibody and the anti-NKG2A antibody are administered by i.v. In one embodiment the anti-PD-1 or anti-PD-L1 antibody and the anti-NKG2A antibody are administered on the same day, optionally further once about every two weeks, optionally further by i.v.

In other aspects, methods are provided for identifying NKG2A+PD1+NK cells and/or T cells. Assessing the co-expression of NKG2A and PD-1 on NK cells and/or T cells can be used in diagnostic or prognostic methods. For example, a biological sample can be obtained from an individual (e.g. from cancer or cancer-adjacent tissue obtained from a cancer patient) and analyzed for the presence of NKG2A+PD1+NK and/or T cells. The expression of both NKG2A and PD-1 on such cells can, for example, be used to identify individuals having tumor infiltrating NK and/or T cells which are inhibited by both NKG2A and PD1 polypeptides. The method can, for example, be useful as a prognostic for response to treatment with an agent that neutralizes NKG2A, as a prognostic for response to treatment with an agent that neutralizes PD1, or as a prognostic for response for combined treatment with an agent that neutralizes NKG2A and an agent that neutralizes PD1.

In one embodiment, provided is a method for assessing whether an individual is suitable for treatment with an agent that inhibits NKG2A and an agent that neutralizes the inhibitory activity of human PD-1, the method comprising detecting a lymphocyte population (e.g. CD8+ T cells) that express both an NKG2A nucleic acid or polypeptide and a PD-1 nucleic acid or polypeptide in a biological sample from an individual. A determination that the individual has a lymphocyte population that express both an NKG2A nucleic acid or polypeptide and a PD-1 nucleic acid or polypeptide indicates that the patient has a cancer that can be treated with an agent that inhibits NKG2A in combination with an agent that neutralizes the inhibitory activity of human PD-1.

In other aspects, methods are provided for identifying NKG2A+PD1+NK cells and/or T cells. The finding that tumor infiltrating effector lymphocytes can express both inhibitory receptors NKG2A and PD-1 gives rise to improved treatment methods as well as methods to detect such double-restricted/inhibited effector cells that can be useful in diagnostics and prognostics.

For example, a biological sample can be obtained from an individual (e.g. from cancer or cancer-adjacent tissue obtained from a cancer patient) and analyzed for the presence of NKG2A+PD1+NK and/or T cells. The expression of both NKG2A and PD-1 on such cells can, for example, be used to identify individuals having tumor infiltrating NK and/or T cells which are inhibited by both NKG2A and PD1 polypeptides. The method can, for example, be useful as a prognostic for response to treatment with an agent that neutralizes NKG2A, as a prognostic for response to treatment with an agent that neutralizes PD1, or as a prognostic for response for combined treatment with an agent that neutralizes NKG2A and an agent that neutralizes PD1.

Detecting NKG2A- and PD-1 restricted NK and/or CD8 T cells within biological samples can more generally have advantages for use in the study, evaluation, diagnosis, prognosis and/or prediction of pathologies where characterization of NK and/or CD8 T cells is of interest. For example, favorable or unfavorable cancer prognosis can be made by assessing whether tumor or tumor adjacent tissues are characterized by infiltrating NK and/or CD8 T cells that express both NKG2A and PD-1.

For example, cancer in patients can be characterized or assessed using anti-NKG2A and anti-PD1 antibodies to assess whether tumor-infiltrating NK and/or CD8 T cells are NKG2A+PD1+, including whether such NK and/or CD8 T cells are present at the tumor periphery (in cancer adjacent tissue). The methods can be useful to determine whether a patient has a pathology characterized by NK and/or CD8 T cells which could be amenable to modulation by therapeutic agents that directly act on such NK and/or CD8 T cells (e.g. by binding to NKG2A and/or PD-1, or their respective ligands HLA-E or PD-L1) or that indirectly act on such NK and/or CD8 T cells (e.g., by producing cytokines or other signalling molecules that can modulate the activity of the NK and/or CD8 T cells). Optionally, in any embodiment, the patient has been treated with an agent that neutralizes PD-1. The methods described herein can optionally further comprise administering to an individual such a therapeutic agent if it determined that the individual has a pathology which could be amenable to modulation by therapeutic agents that act on the tumor infiltrating NK and/or CD8 T cells.

In one aspect the inventors provides an in vitro method for detecting a NKG2A+PD1+ lymphocyte, optionally an NK or CD8+ T cell, the method comprising providing a biological sample comprising tumor infiltrating lymphocytes and determining whether the lymphocytes express NKG2A and PD-1.

In one aspect the inventors provides an in vitro method of detecting NKG2A and PD1-expressing (i.e. double positive) CD8 T cells or NK cells within a sample from a human individual, said method comprising providing a sample from an individual, contacting cells in said sample using a monoclonal antibody that specifically binds to a human NKG2A polypeptide and a monoclonal antibody that specifically binds to a human PD-1 polypeptide in the samples, and detecting binding of the antibodies to cells. In one embodiment the cells are CD8 T cells and/or NK cells.

In one aspect the inventors provides an in vitro method of detecting tissue infiltrating human CD8 T cells and/or NK cells that are inhibited by both NKG2A and PD-1 within a sample from a human individual, said method comprising providing a sample from an individual, and detecting tissue infiltrating CD8 T cells and/or NK cells in said sample using a monoclonal antibody that specifically binds to a human NKG2A polypeptide and a monoclonal antibody that specifically binds to a human PD-1 polypeptide in the samples, wherein a detection of NKG2A and PD-1 polypeptide indicates the presence of NKG2A- and PD-1-inhibited tissue infiltrating CD8 T cells and/or NK cells. Optionally, in any embodiment, the patient has been treated with an agent that neutralizes PD-1. In one embodiment, the sample comprises tumor cells, tumor tissue or tumor adjacent tissue. In one embodiment, the CD8 T cells and/or NK cells are identified using immunohistochemistry methods. In one embodiment, the sample is a paraffin-embedded sample; optionally the paraffin-embedded sample has been fixed, embedded in paraffin, sectioned, deparaffinized, and transferred to a slide before being brought into contact with the monoclonal antibody. In one embodiment, the CD8 T cells and/or NK cells are identified using flow cytometry methods.

Examples

Example 1—RMA-S and A20 Tumor Cells are Infiltrated by NK Cells Expressing NKG2A and CD8 T Cells Expressing NKG2A and/or PD-1

Lymphocytes generally are not found to co-express NKG2A and PD-1. To investigate the expression of these receptors on tumor-infiltrating lymphocytes, distribution of NKG2A and PD-1 were studied on NK and T cell subsets in tumor from mice. Lymphocytes were taken from spleen, from tumor draining lymph nodes, as well as from within solid tumors.

C57/BL6 mice were engrafted (sc) with PDL-1+Qa-1+ RMA-S cells (Qa-1, Qdm, B2m) or with A20 tumor cells. RMA-S Qa-1 Qdm B2m (top row) and A20 (bottom row) tumor bearing mice were sacrificed when tumor volumes were around 500 $mm^3$.

Figure 1B:
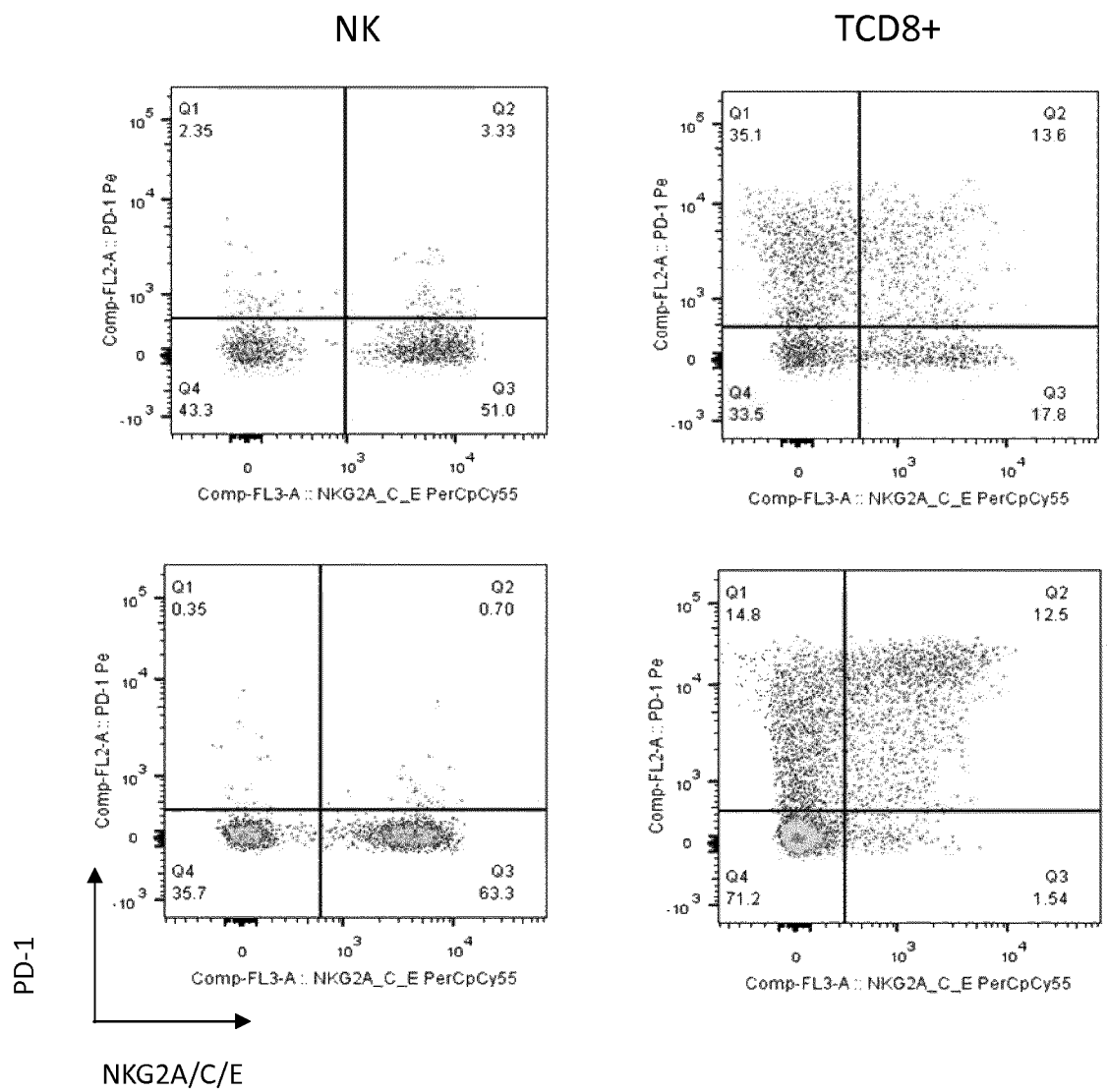

Results are shown in FIGS. 1A and 1B. Tumor cells (FIG. 1 A) and tumor infiltrating lymphocytes-TIL- (FIG. 1 B) were analyzed by flow cytometry respectively for the expression of Qa-1 and PDL-1 for tumor cells and NKG2A and PD-1 for TIL. One representative mouse out of 3 is shown. MFI:Median of fluorescence intensity.

More than half of the infiltrating NK cells from both tumor types expressed NKG2A, suggesting that tumor-infiltrating NK cells are inhibited by NKG2A. The NKG2A+ NK cells generally did not express significant amounts of PD-1. However, CD8 T cells that were positive for both NKG2A and PD-1 were found, suggesting that the CD8 T cells may be restricted by both inhibitory receptors NKG2A and PD-1.

Example 2—NK and T Cell Subsets from Mice Bearing Rma-Rae1 Tumors are Capable of NKG2A and PD-1 Co-Expression To further investigate the expression of receptors NKG2A and PD-1, distribution of NKG2A and PD-1 were studied on NK and T cell subsets in mice. Lymphocytes were taken from spleen, from tumor draining lymph nodes, as well as from within solid tumors.

C57/BL6 mice were engrafted (sc) with RMA-Rae clone 6 (2 million cells). These tumor cells express CD94/NKG2A ligand, Qa-1. Mice were sacrificed at day 12 with a mean tumor volume: 723 $mm^3$, SD: 161 $mm^3$, n=4. Following cell suspension preparation from spleen, LN and tumor, cells were stained as follows: CD3e PerCP Cy5.5, NKP46 Alexa 647, NKG2A/C/E FITC, PD1 PE, CD8 Pacific Blue.

Figure 2:
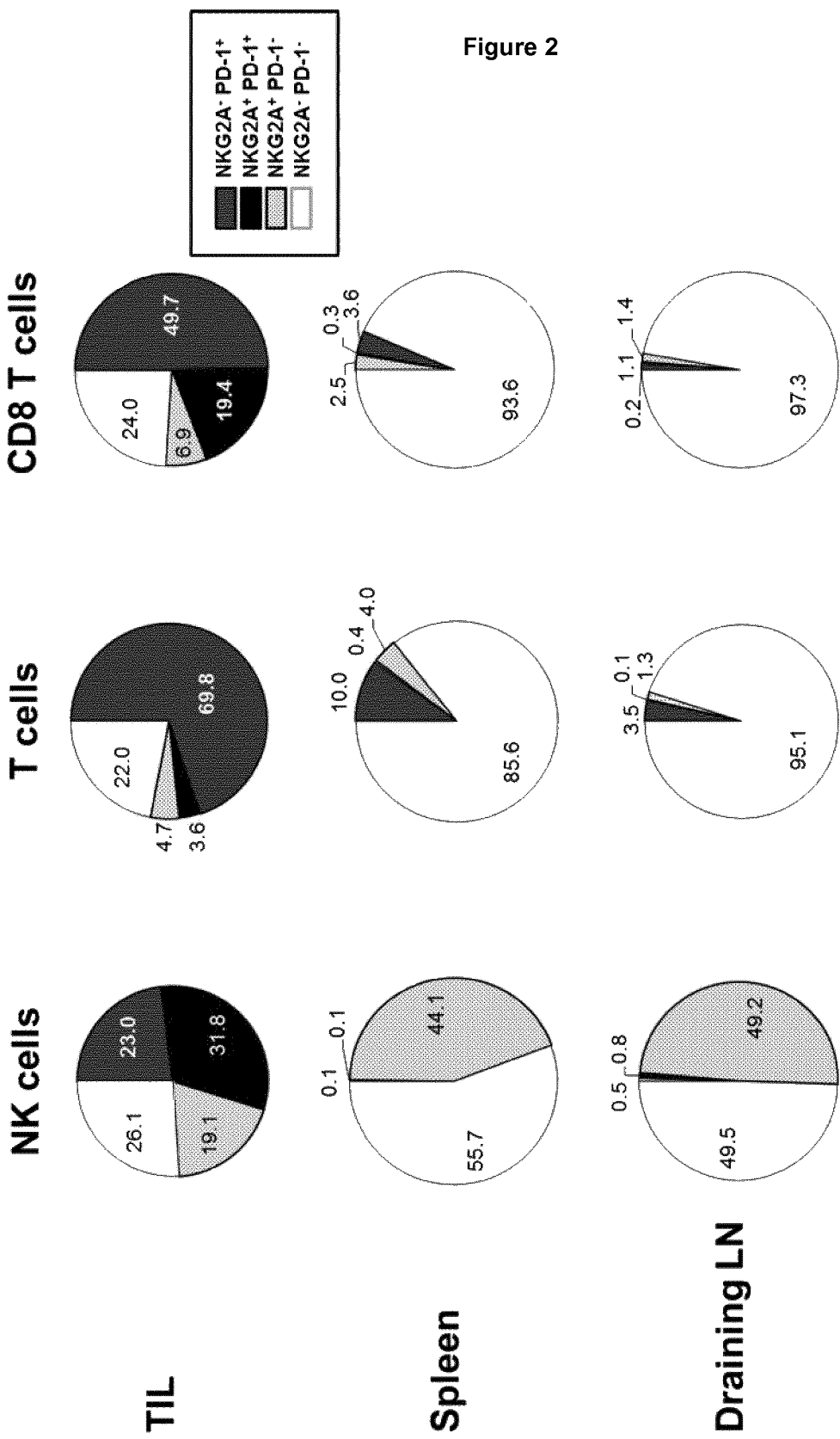
FIG. 2 shows distribution of NKG2A and PD-1 on NK and T cell subsets in mice. Lymphocytes were taken from spleen, from tumor draining lymph nodes, and from within solid tumor masses. PD-1 expression was infrequent or absent among all cell subsets from spleen and lymph nodes, however among tumor infiltrating lymphocytes (TIL), all cells subsets had relatively high percentages of cells expressing PD-1. NKG2A on the other hand was found on NK cells but not on T cell subsets in spleen and lymph nodes, yet in the tumor was found on a significant percentage of the TILs, with a mean of more than 30% of NK cells and more than 19% of CD8 T cells double positive for NKG2A and PD-1.

Results are shown in FIG. 2 and Tables 1-3.

In the NK cell subset, cells in both the draining lymph nodes and spleen were about half NKG2A-positive and half NKG2A-negative, however in neither case was there significant expression of PD1. NK cells from lymph nodes were $NKG2A^+PD-1^-$ (49.2%) and $NKG2A^- PD-1^-$ (49.5%), and less than 1% (mean) of NK cells were $NKG2A^+PD-1^+$. NK cells from spleen were $NKG2A^+PD-1^-$ (44.1%) and $NKG2A^- PD-1^-$ (55.7%) and a mean of 0.1% (mean) of NK cells were $NKG2A^+PD-1^+$.

In the T cell subset most cells were NKG2A-negative (only 1.1% in lymph nodes and 4.7% in spleen are $NKG2A^+$), and a small fraction of cells were $PD-1^+$ (3.5% in lymph nodes and 10% in spleen were $PD-1^+ NKG2A^-$), without significant double positive NKG2A PD-1 cells. Only 0.1% (mean) of T cells in lymph nodes were $NKG2A^+ PD-1^+$ and only 0.4% (mean) of T cells in spleen were $NKG2A^+PD-1^+$. 95.1% of T cells from lymph nodes were double negative and 85.6% of T cells from spleen were double negative.

In the CD8 T cell subset, most cells were again NKG2A-negative (only 1.6% in lymph nodes and 3.9% in spleen are $NKG2A^+$), and a small fraction of cells were $PD-1^+$ (1.1% in lymph nodes and 2.5% in spleen were $PD-1^+ NKG2A^-$), without significant double positive NKG2A PD-1 cells. Only 0.2% (mean) of T cells in lymph nodes were $NKG2A^+$ $PD-1^+$ and only 0.3% (mean) of T cells in spleen were $NKG2A^+PD-1^+$. 97.3% of T cells from lymph nodes were double negative and 93.6% of T cells from spleen were double negative.

However, among tumor infiltrating lymphocytes (TIL), all cells subsets had cells expressing PD-1. NK cells, which were not previously found in significant percentages to express PD-1, were observed in tumor to be PD-1-positive, including within the $NKG2A^+$ subset, with 31.8% (mean) of NK cells that were $NKG2A^+PD-1^+$. While almost no CD8 T cells outside the tumor had NKG2A expression, CD8 T cells expressing PD-1 were frequent in the tumor (the tumor infiltrating CD8 T cell subset had a mean of 26.3% NKG2A+ positive cells). Moreover, within this NKG2A-positive CD8 T cell subset, most of the cells were $NKG2A^+$ $PD1^+$ (19.4% (mean)). Yet, among the $CD8^-$ T cell subset, there was little difference in NKG2A expression observed between TILs and spleen or lymph node cells, as only 5.1% of T cells in the tumor expressed NKG2A, and only 3.6% of T cells were double positive NKG2A PD-1.

TABLE 1

| Spleen | | | | | |
|---|---|---|---|---|---|
| % among NK | | | | | |
| | % NK NKG2A− PD1+ | % NK NKG2A+ PD1+ | % NK NKG2A+ PD1− | % NK NKG2A− PD1− | % NK NKG2A+ |
| Mice1 Spleen | 0.064 | 0.064 | 41.8 | 58.1 | 41.864 |
| Mice2 Spleen | 0.15 | 0.098 | 46.1 | 53.7 | 46.198 |
| Mice4 Spleen | 0.19 | 0.19 | 44.3 | 55.3 | 44.49 |
| Mean | 0.1 | 0.1 | 44.1 | 55.7 | 44.2 |
| SD | 0.1 | 0.1 | 2.2 | 2.2 | 2.2 |
| % among T lymphocytes | | | | | |
| | % T NKG2A− PD1+ | % T NKG2A+ PD1+ | % T NKG2A+ PD1− | % T NKG2A− PD1− | % T NKG2A+ |
| Mice1 Spleen | 8.08 | 0.38 | 4.52 | 87 | 4.54 |
| Mice2 Spleen | 9.64 | 0.32 | 4.22 | 85.8 | 6.25 |
| Mice4 Spleen | 12.3 | 0.41 | 3.21 | 84.1 | 3.37 |
| Mean | 10.0 | 0.4 | 4.0 | 85.6 | 4.7 |
| SD | 2.13 | 0.05 | 0.69 | 1.46 | 1.45 |
| % among CD8+ T lymphocytes | | | | | |
| | % TCD8+ NKG2A− PD1+ | % TCD8+ NKG2A+ PD1+ | % TCD8+ NKG2A+ PD1− | % TCD8+ NKG2A− PD1− | % T CD8+ NKG2A+ |
| Mice1 Spleen | 1.8 | 0.27 | 4.68 | 93.2 | 4.95 |
| Mice2 Spleen | 2.08 | 0.27 | 3.09 | 94.6 | 3.36 |
| Mice4 Spleen | 3.67 | 0.48 | 2.97 | 92.9 | 3.45 |
| Mean | 2.5 | 0.3 | 3.6 | 93.6 | 3.9 |
| SD | 1.01 | 0.12 | 0.95 | 0.91 | 0.89 |

TABLE 2

Tumor Draining Lymph Nodes

% among NK

| | % NK NKG2A− PD1+ | % NK NKG2A+ PD1+ | %NK NKG2A+ PD1− | % NK NKG2A− PD1− | % NK NKG2A+ |
|---|---|---|---|---|---|
| Mice1 LN | 0.68 | 0.85 | 45.10 | 53.40 | 45.95 |
| Mice3 LN | 0.20 | 0.40 | 54.70 | 44.70 | 55.10 |
| Mice4 LN | 0.61 | 1.21 | 47.90 | 50.30 | 49.11 |
| Mean | 0.50 | 0.82 | 49.23 | 49.47 | 50.05 |
| SD | 0.26 | 0.41 | 4.94 | 4.41 | 4.65 |

% among T lymphocytes

| | % T NKG2A− PD1+ | % T NKG2A+ PD1+ | % T NKG2A+ PD1− | % T NKG2A− PD1− | % T NKG2A+ |
|---|---|---|---|---|---|
| Mice1 LN | 2.8 | 0.1 | 1.8 | 95.3 | 0.5 |
| Mice3 LN | 6.6 | 0.4 | 2.4 | 90.6 | 0.7 |
| Mice4 LN | 2.1 | 0.0 | 0.6 | 97.2 | 0.6 |
| Mean | 3.5 | 0.1 | 1.3 | 95.1 | 1.1 |
| SD | 2.1 | 0.2 | 0.9 | 3.1 | 1.1 |

% among CD8+ T lymphocytes

| | % TCD8+ NKG2A− PD1+ | % TCD8+ NKG2A+ PD1+ | % TCD8+ NKG2A+ PD1− | % TCD8+ NKG2A− PD1− | % T CD8+ NKG2A+ |
|---|---|---|---|---|---|
| Mice1 LN | 1.0 | 0.2 | 2.0 | 96.8 | 2.1 |
| Mice3 LN | 2.1 | 0.6 | 2.5 | 94.8 | 3.1 |
| Mice4 LN | 0.6 | 0.1 | 0.7 | 98.6 | 0.8 |
| Mean | 1.1 | 0.2 | 1.4 | 97.3 | 1.6 |
| SD | 0.7 | 0.3 | 1.0 | 1.9 | 1.3 |

TABLE 3

Tumor Infiltrating Lymphocytes

% among NK

| | % NK NKG2A− PD1+ | % NK NKG2A+ PD1+ | % NK NKG2A+ PD1− | % NK NKG2A− PD1− | % NK NKG2A+ |
|---|---|---|---|---|---|
| Mice1 TIL | 18.8 | 25.6 | 26.6 | 28.9 | 52.2 |
| Mice2 TIL | 22.8 | 31 | 13.5 | 32.7 | 44.5 |
| Mice3 TIL | 26 | 38.2 | 13.8 | 22 | 52 |
| Mice4 TIL | 24.4 | 32.5 | 22.5 | 20.7 | 55 |
| Mean | 23 | 31.8 | 19.1 | 26.1 | 50.9 |
| SD | 3.1 | 5.2 | 6.5 | 5.7 | 4.5 |

% among T lymphocytes

| | % T NKG2A− PD1+ | % T NKG2A+ PD1+ | % T NKG2A+ PD1− | % T NKG2A− PD1− | % T NKG2A+ |
|---|---|---|---|---|---|
| Mice1 TIL | 51.7 | 4.85 | 7.8 | 35.6 | 2.89 |
| Mice2 TIL | 86.5 | 1.47 | 1.42 | 10.7 | 8.22 |
| Mice3 TIL | 75 | 4.93 | 3.29 | 16.8 | 9.3 |
| Mice4 TIL | 66 | 3.1 | 6.2 | 24.7 | 0 |
| Mean | 69.8 | 3.6 | 4.7 | 22.0 | 5.1 |
| SD | 14.7 | 1.6 | 2.9 | 10.8 | 4.4 |

% among CD8+ T lymphocytes

| | % TCD8+ NKG2A− PD1+ | % TCD8+ NKG2A+ PD1+ | % TCD8+ NKG2A+ PD1− | % TCD8+ NKG2A− PD1− | % T CD8+ NKG2A+ |
|---|---|---|---|---|---|
| Mice1 TIL | 49.5 | 16 | 10.8 | 23.7 | 26.8 |
| Mice2 TIL | 52.2 | 21.7 | 4.35 | 21.7 | 26.05 |
| Mice3 TIL | 44.3 | 28.6 | 5.71 | 21.4 | 34.31 |
| Mice4 TIL | 52.8 | 11.3 | 6.6 | 29.2 | 17.9 |
| Mean | 49.7 | 19.4 | 6.9 | 24.0 | 26.3 |
| SD | 3.9 | 7.5 | 2.8 | 3.6 | 6.7 |

Example 3—NKG2A and PD-1 Expression in Tumor Bearing Mice

To further investigate NKG2A and PD-1 expression in tumor-bearing mice, C57/BL6 mice were engrafted (sc) with different tumor cells, either RMA-Rae1, MC38 or RMA lines. To evaluate the influence of tumor volume, mice were sacrificed when their tumors reached respectively the volumes of 500, 2000 and 800 mm$^3$.

Results are shown in FIGS. 3A and 3B, with RMA Rae1 (top row), MC38 (medium row) and RMA (bottom row). NK cells (FIG. 3A) and CD8 T cells (FIG. 3B) were analyzed by flow cytometry in spleen, tumor draining lymph node (LN) and tumor for NKG2A and PD-1 expression. One representative mouse out of 2 to 4 is shown.

In the NK cell subset, cells in the tumor, lymph nodes and spleen were about half NKG2A-positive and half NKG2A-negative. Neither NK cells (regardless of their NKG2A expression) from the draining lymph nodes nor the spleen showed any significant expression of PD1. However, the tumor infiltrating NK cells from RMA-Rae1 and RMA expressed significant levels of both NKG2A and PD1. Tumor infiltrating NK cells from tumor line MC38 that were sacrificed with particularly large volume (2000 mm$^3$) expressed NKG2A (50%) but did not significantly express PD1 (3%).

Unlike NK cells which express NKG2A in about half the population, the CD8 T cells from spleen and lymph nodes generally expressed neither NKG2A nor PD1. However, in tumors, a large proportion of CD8 T cells expressed both NKG2A and PD1 (28% in RMA-Rae1, 43% of MC38 and 40% of RMA were double positive). The results again suggest that tumor infiltrating CD8 T cells as well as NK cells may be capable of being restricted by both inhibitory receptor NKG2A and PD1, furthermore across different types of tumor cells.

Example 4—Treatment with Anti-PD-1 mAb Increases the Frequency of NKG2A Expressing CD8 T Cells in Tumors To evaluate the effect of treatment with anti-PD1 antibody on CD8 T cells, MC38 tumor bearing mice were either treated with 200 μg of rat IgG2a isotype control (IC) or neutralizing anti-mouse PD-1 monoclonal antibodies on days 11, 14 and 17 after cells engraftment. Mice (n=3/group) were sacrificed on day 31 and CD8 T cells were characterized by flow cytometry in spleen, tumor draining lymph node (LN) and tumor. Means+/−SD (n=3) of the percentages of CD8 NKG2A+ among CD8 T cells are represented. $P<0.005$ (*), $P<0.0005$ (**), statistical analysis performed with Two way ANOVA followed by Tukey's multiple comparison test.

Figure 4:
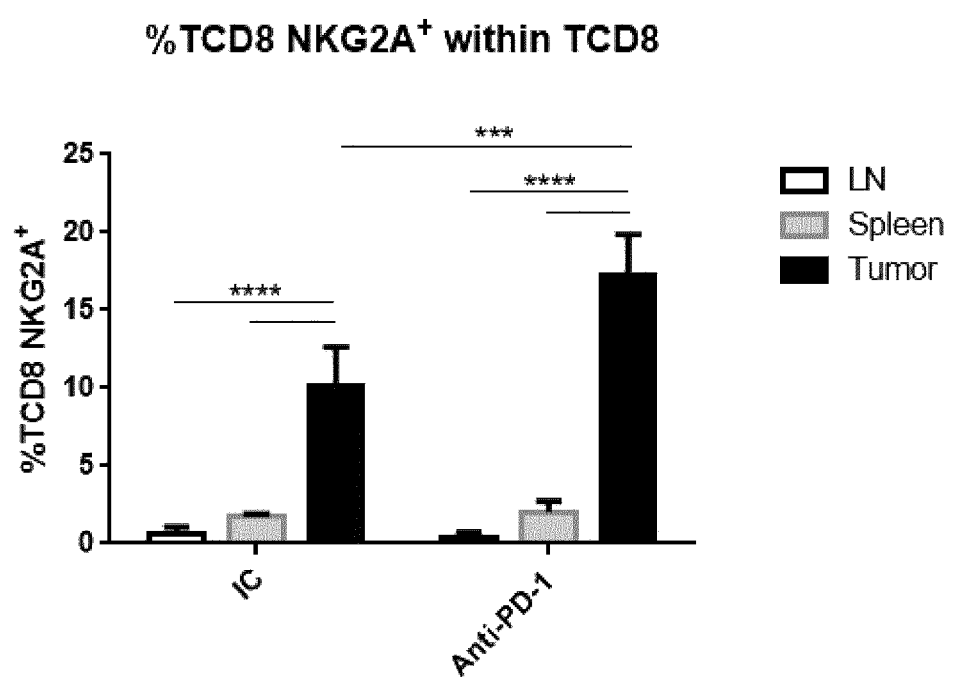
FIG. 4 shows treatment of mice with anti-PD-1 mAb increases the frequency of NKG2A expressing TCD8 cells in MC38 tumors. MC38 tumor bearing mice were either treated with 200 μg of rat IgG2a isotype control (IC) or anti-mouse PD-1 antibodies on days 11, 14 and 17 after cells engraftment. Mice were sacrificed on day 31 and CD8 T cells were characterized by flow cytometry in spleen, tumor draining lymph node (LN) and tumor.

Results are shown in FIG. 4. Similarly to that observed in other experiments, CD8 T cells from spleen of lymph nodes did not significantly express NKG2A. Administration of anti-PD1 antibody did not cause any change in the level of NKG2A expression in the spleen or lymph node T cells.

However, in the tumor infiltrating CD8 T cell population, administration of anti-PD1 antibody caused a more than 50% increase in NKG2A-expressing CD8 T cells. The results suggest that upon treatment with anti-PD1 antibody, NKG2A receptor may have an increased contribution to the inhibition of the CD8 T cell response toward tumors in vivo. Neutralization of NKG2A may therefore be useful to reverse the inhibition of the NKG2A restricted T cells in individuals treated with an agent that neutralizes the PD-1 axis such as an anti-PD1 or PDL1 antibody.

Example 5—Combinatorial Anti-NKG2A/Anti-PD1 Blockade Inhibits Tumor Growth

To evaluate the effect of combination treatment with neutralizing anti-PD1 antibody and neutralizing anti-NKG2A antibody, C57BL/6 mice were engrafted (sc) with RMA-S Qa-1 Qdm B2m tumor cells and treated with neutralizing anti-PD1 agent (a neutralizing anti-PD-L1 antibody) and neutralizing anti-NKG2A antibody.

Briefly, C57BL/6 mice were randomized on day 11 when RMA-S Qa-1 Qdm B2m tumor volume were about 85 $mm^3$ (n=8 mice/group) and treated with isotype control, anti-mouse NKG2A mAb (200 μg, iv), anti-mouse PD-L1 mAb (200 μg, ip) or anti-mNKG2A/mPDL-1 combination on days 11, 14 and 18. Tumor volume was measured twice a week with a caliper. Animals were euthanized when tumor became large (volume >2000 $mm^3$), ulcerated or necrotic. Data represent median tumor volume per experiment.

Figure 5:
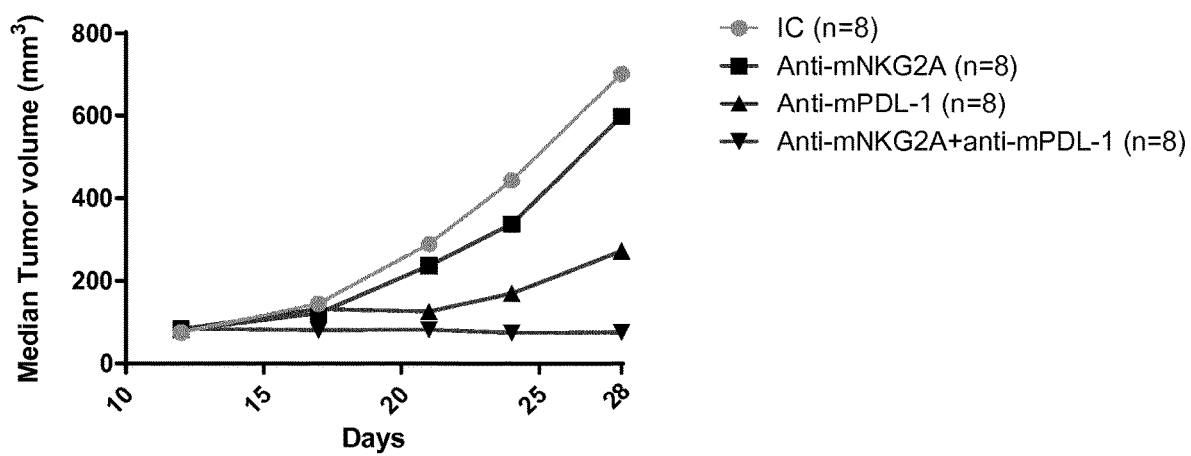
FIG. 5 shows median tumor volume over time in mice treated with isotype control, anti-mouse NKG2A mAb (200 μg, iv), anti-mouse PD-L1 mAb (200 μg, ip) or anti-mNKG2A/mPDL-1 combination on days 11, 14 and 18. While anti-NKG2A yielded only a modest anti-tumor effect compared to isotype control in this model and anti-PD-L1 yielded a substantial anti-tumor effect but with tumor volume increasing toward day 28, the combined treatment with anti-NKG2A and anti-PD-L1 completely abolished tumor growth, with no significant growth in tumor volume observed at day 28.

The evolution of median tumor volume over time is shown in FIG. 5. While anti-NKG2A yielded only a modest anti-tumor effect compared to isotype control in this model and anti-PD-L1 yielded a substantial anti-tumor effect but with tumor volume increasing toward day 28, the combined treatment with anti-NKG2A and anti-PD-L1 completely abolished tumor growth, with no significant growth in tumor volume observed at day 28.

All references, including publications, patent applications, and patents, cited herein are hereby incorporated by reference in their entirety and to the same extent as if each reference were individually and specifically indicated to be incorporated by reference and were set forth in its entirety herein (to the maximum extent permitted by law), regardless of any separately provided incorporation of particular documents made elsewhere herein.

The use of the terms "a" and "an" and "the" and similar referents in the context of describing the invention are to be construed to cover both the singular and the plural, unless otherwise indicated herein or clearly contradicted by context.

Unless otherwise stated, all exact values provided herein are representative of corresponding approximate values (e.g., all exact exemplary values provided with respect to a particular factor or measurement can be considered to also provide a corresponding approximate measurement, modified by "about," where appropriate). Where "about" is used in connection with a number, this can be specified as including values corresponding to +1-10% of the specified number.

The description herein of any aspect or embodiment of the invention using terms such as "comprising", "having," "including," or "containing" with reference to an element or elements is intended to provide support for a similar aspect or embodiment of the invention that "consists of", "consists essentially of", or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context).

The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

---

The invention claimed is:

1. A method of treating a cancer in a human patient, the method comprising administering to the patient an effective amount of each of: (a) an antibody that neutralizes human NKG2A, and (b) an antibody that neutralizes human PD-L1, wherein the antibody that neutralizes human NKG2A comprises the CDR1, CDR2 and CDR3 domains of a heavy chain having the sequence set forth in any one of SEQ ID NOS: 4-8, and the CDR1, CDR2 and CDR3 domains of a light chain having the sequence set forth in SEQ ID NO: 9 and the antibody that neutralizes human PD-L1 is selected from nivolumab, lambrolizumab, pembrolizumab, atezolizumab, or pidlizumab.

2. The method of claim 1, wherein at least two doses of the antibody that neutralizes human NKG2A are administered in an amount effective to achieve a continuous blood concentration of anti-NKG2A antibody of at least 10 µg/ml for at least one week following administration thereof.

3. The method of claim 2, wherein the method comprises at least one administration cycle, wherein for each cycle, two, three or four doses of the antibody that neutralizes human NKG2A are administered and two, three or four doses of the antibody that neutralizes human PD-L1 are administered.

4. The method of claim 1, wherein the antibody that neutralizes human NKG2A and the antibody that neutralizes human PD-L1 are formulated for separate administration and are administered concurrently or sequentially.

5. The method of claim 1, wherein the antibody that neutralizes human NKG2A and the antibody that neutralizes human PD-L1 are formulated in a single formulation.

6. The method of claim 1, wherein the antibody that neutralizes human NKG2A and the antibody that neutralizes human PD-L1 are administered on the same day.

7. The method of claim 1, wherein the cancer is a solid tumor.

8. The method of claim 1, wherein the cancer is hematological tumor.

9. The method of claim 7, wherein the cancer is selected from the group consisting of lung cancer, renal cell carcinoma (RCC), melanoma, colorectal cancer, and ovarian cancer.

10. The method of claim 1, wherein the cancer is an HLA-E-expressing cancer.

11. The method of claim 1, wherein said antibody that neutralizes human NKG2A is a non-depleting antibody.

12. The method of claim 11, wherein said antibody is IgG4 antibody, wherein said antibody lacks an Fc domain or wherein said antibody comprises an Fc domain that is modified to reduce binding between the Fc domain and an Fcγ receptor.

13. The method of claim 3, wherein the administration cycle comprises a period of eight weeks.

* * * * *

UNITED STATES PATENT AND TRADEMARK OFFICE
CERTIFICATE OF CORRECTION

PATENT NO. : 10,711,063 B2
APPLICATION NO. : 15/511778
DATED : July 14, 2020
INVENTOR(S) : Pascale Andre et al.

Page 1 of 1

It is certified that error appears in the above-identified patent and that said Letters Patent is hereby corrected as shown below:

In the Specification

<u>Column 1,</u>
Line 50, "Ca'" should read --$Ca^{++}$--.

<u>Column 21,</u>
Line 26, "0801470SPD-L-I" should read --0801470_SPD-L-I--.

In the Claims

<u>Column 64,</u>
Line 31, "Fey receptor." should read --Fcγ receptor.--.

Signed and Sealed this
Seventeenth Day of November, 2020

Andrei Iancu
*Director of the United States Patent and Trademark Office*